(12) United States Patent
Boyle et al.

(10) Patent No.: US 11,160,924 B2
(45) Date of Patent: Nov. 2, 2021

(54) FLUID INFUSION SYSTEM

(71) Applicant: Covidien LP, Mansfield, MA (US)

(72) Inventors: Peter Boyle, Bedford, NH (US); Keith Isaacson, Newton, MA (US); Seth Traub, Andover, MA (US); Craig Traub, Andover, MA (US)

(73) Assignee: Covidien LP, Mansfield, MA (US)

( * ) Notice: Subject to any disclaimer, the term of this patent is extended or adjusted under 35 U.S.C. 154(b) by 2 days.

(21) Appl. No.: 16/219,367

(22) Filed: Dec. 13, 2018

(65) Prior Publication Data
US 2020/0139045 A1    May 7, 2020

Related U.S. Application Data

(63) Continuation of application No. 15/199,274, filed on Jun. 30, 2016, now Pat. No. 10,159,790.
(Continued)

(51) Int. Cl.
*A61M 1/00* (2006.01)
*A61M 5/172* (2006.01)
(Continued)

(52) U.S. Cl.
CPC .............. *A61M 5/172* (2013.01); *A61B 17/42* (2013.01); *A61B 46/00* (2016.02); *A61B 46/30* (2016.02);
(Continued)

(58) Field of Classification Search
CPC ...... A61M 1/0035; A61M 2005/14506; A61M 5/1415; A61M 5/16813; A61M 5/445;
(Continued)

(56) References Cited

U.S. PATENT DOCUMENTS

| 4,295,631 A | 10/1981 | Allen |
|---|---|---|
| 4,730,188 A | 3/1988 | Milheiser |

(Continued)

FOREIGN PATENT DOCUMENTS

WO    2014102537 A1    7/2014

*Primary Examiner* — Rebecca E Eisenberg
(74) *Attorney, Agent, or Firm* — Carter, DeLuca & Farrell LLP

(57) ABSTRACT

A fluid infusion system includes an air pump connected to an accumulator tank to produce pressurized air that is stored in the accumulator tank. The system can include one or more fluid bag chambers wherein each fluid bag chamber includes an inflatable bladder positioned inside the fluid bag chamber to apply pressure on the fluid bag supported inside the chamber. The fluid bag can be connected by a tube set to deliver fluid from the fluid bag to a surgical tool at a surgical site. The fluid can, for example, be irrigation fluid or distention fluid. The system can include a controller connected to the pump to control the pump to produce the pressurized air and an adjustable pressure regulator can be connected between the accumulator tank and the inflatable bladder to control the pressure of air delivered to the inflatable bladder and the pressure that the fluid is delivered to the surgical tool. A pressure sensor can be connected between the adjustable pressure regulator and the inflatable bladder to measure the air pressure delivered to the inflatable bladder and send the air pressure measurements to the controller. The controller can configure the system display to show the air pressure measured by the pressure sensor.

19 Claims, 13 Drawing Sheets

Related U.S. Application Data

(60) Provisional application No. 62/187,162, filed on Jun. 30, 2015.

(51) Int. Cl.
*A61M 5/14* (2006.01)
*A61M 5/148* (2006.01)
*A61M 5/168* (2006.01)
*A61M 5/44* (2006.01)
*A61M 3/02* (2006.01)
*A61B 17/42* (2006.01)
*A61B 46/00* (2016.01)
*A61B 90/96* (2016.01)
*A61B 90/98* (2016.01)
*A61M 5/145* (2006.01)
*A61B 50/13* (2016.01)
*A61B 46/23* (2016.01)
*A61F 7/00* (2006.01)

(52) U.S. Cl.
CPC .............. *A61B 90/96* (2016.02); *A61B 90/98* (2016.02); *A61M 1/777* (2021.05); *A61M 3/0216* (2014.02); *A61M 3/0258* (2013.01); *A61M 5/1407* (2013.01); *A61M 5/1415* (2013.01); *A61M 5/1486* (2013.01); *A61M 5/16813* (2013.01); *A61M 5/445* (2013.01); *A61B 50/13* (2016.02); *A61B 2017/4216* (2013.01); *A61B 2046/236* (2016.02); *A61B 2217/005* (2013.01); *A61B 2217/007* (2013.01); *A61F 2007/0059* (2013.01); *A61M 1/743* (2021.05); *A61M 1/84* (2021.05); *A61M 2005/14506* (2013.01); *A61M 2205/15* (2013.01); *A61M 2205/18* (2013.01); *A61M 2205/3334* (2013.01); *A61M 2205/3368* (2013.01); *A61M 2205/3389* (2013.01); *A61M 2205/50* (2013.01); *A61M 2205/502* (2013.01); *A61M 2205/505* (2013.01); *A61M 2205/52* (2013.01); *A61M 2205/6072* (2013.01); *A61M 2205/8206* (2013.01)

(58) Field of Classification Search
CPC .............. A61M 1/006; A61M 2205/15; A61M 2205/18; A61M 2205/3334; A61M 2205/3368; A61M 2205/3389; A61M 2205/505; A61M 2205/52; A61M 2205/6072; A61M 3/0216
See application file for complete search history.

(56) References Cited

U.S. PATENT DOCUMENTS

| | | | |
|---|---|---|---|
| 4,759,349 A | 7/1988 | Betz et al. | |
| 5,207,645 A | 5/1993 | Ross et al. | |
| 5,709,670 A | 1/1998 | Vancaillie et al. | |
| 5,733,263 A | 3/1998 | Wheatman | |
| 5,772,634 A | 6/1998 | Atkinson | |
| 5,814,009 A | 9/1998 | Wheatman | |
| 6,024,142 A | 2/2000 | Bates | |
| 6,085,805 A | 7/2000 | Bates | |
| 6,135,989 A | 10/2000 | Atad et al. | |
| 6,641,556 B1 | 11/2003 | Shigezawa | |
| 6,824,528 B1 * | 11/2004 | Faries, Jr. | A61M 5/148 604/113 |
| 7,351,226 B1 | 4/2008 | Herskowitz | |
| 7,604,610 B2 | 10/2009 | Shener et al. | |
| 7,825,812 B2 | 11/2010 | Ogrin et al. | |
| D657,865 S | 4/2012 | Williams | |
| 8,597,228 B2 | 12/2013 | Pyles et al. | |
| 8,708,950 B2 * | 4/2014 | Scarpaci | A61M 1/3656 604/28 |
| 8,790,303 B2 | 7/2014 | Williams et al. | |
| 9,642,737 B2 | 5/2017 | Seres et al. | |
| 10,159,790 B2 | 12/2018 | Boyle et al. | |
| 10,201,647 B2 * | 2/2019 | Norris | A61M 1/282 |
| 2004/0170409 A1 | 9/2004 | Faries et al. | |
| 2006/0073048 A1 * | 4/2006 | Malackowski | A61M 3/0258 417/474 |
| 2007/0056983 A1 | 3/2007 | Wells | |
| 2007/0078370 A1 | 4/2007 | Shener et al. | |
| 2009/0131863 A1 | 5/2009 | Carlisle et al. | |
| 2011/0015504 A1 | 1/2011 | Yoo | |
| 2013/0019747 A1 | 1/2013 | Williams et al. | |
| 2016/0051750 A1 * | 2/2016 | Tsoukalis | G16H 40/67 604/151 |
| 2020/0254156 A1 * | 8/2020 | Toth | A61M 1/0031 |

* cited by examiner

FLUID INFUSION SYSTEM

CROSS-REFERENCE TO RELATED APPLICATIONS

This application is a continuation of and claims priority to U.S. patent application Ser. No. 15/199,274, filed, Jun. 30, 2016, which claims benefit under 35 U.S.C. § 119(e) of the U.S. Provisional Application No. 62/187,162, filed Jun. 30, 2015, the contents of all which are incorporated herein by reference in its entirety.

STATEMENT REGARDING FEDERALLY SPONSORED RESEARCH

Not Applicable

REFERENCE TO MICROFICHE APPENDIX

Not Applicable

BACKGROUND

Technical Field of the Invention

The present invention relates to surgery, more particularly, to fluid infusion systems.

Description of the Prior Art

For a variety of reasons, many minimally invasive gynecologic procedures are moving from the operating theater with general anesthesia or intravenous sedation to the office with no or minimal anesthesia. The reasons for this transition include improved efficiency for the patient and physician, reduction in health care cost, and advances in technology that make these procedures well-tolerated in an office setting. Examples of such procedures include diagnostic hysteroscopy, tubal sterilization, and removal of uterine polyps. While equipment is changing, there remains unmet needs including safe delivery and monitoring of fluid distention during hysteroscopic procedures. Currently, systems designed for this function can only be found in the operating room due to size and cost. Likewise, there is a large percentage of hysteroscopic surgical procedures that are currently performed in the operating room that would benefit from a portable, easy to use and cost efficient fluid pump and management system.

SUMMARY

The present invention is directed to a fluid infusion system that can include an air pump connected to an accumulator tank to produce pressurized air that is stored in the accumulator tank and one or more fluid bag chamber, wherein each fluid bag chamber can include an inflatable bladder positioned inside the fluid bag chamber to apply pressure on a fluid bag supported inside the fluid bag chamber. The system can further include a controller connected to the pump to control the pump to produce pressurized air and an adjustable pressure regulator connecting the accumulator tank to the inflatable bladder the control the pressure of the air that is delivered to the inflatable bladder. The system can include a pressure sensors connected between the adjustable pressure regulator and the inflatable bladder configured to measure the air pressure delivered to the inflatable bladder and send the air pressure measurements to the controller and the controller can configure the display to show the air pressure measured by the pressure sensor.

In accordance with some embodiments of the invention, the infusion system can further include a tubing set connected between the fluid bag supported inside the fluid bag chamber and a surgical tool to deliver fluid from the fluid bag to the surgical tool at a predefined pressure that can be adjusted by adjusting the pressure regulator.

In accordance with some embodiments of the invention, the infusion system can further include a volume sensor coupled to the inflatable bladder to produce a measure of inflation of the inflatable bladder and transmit the measure of inflation of the inflatable bladder to the controller.

In accordance with some embodiments of the invention, the infusion system can be configured wherein the controller receives the measure of inflation of the inflatable bladder and determines a measure of volume in the fluid bag as a function of the measure of inflation of the inflatable bladder.

In accordance with some embodiments of the invention, the infusion system can be configured wherein the volume sensor includes a flex sensor coupled to the inflatable bladder and the flex sensor is configured to produce a change in resistance when the flex sensor is flexed as the inflatable bladder is inflated.

In accordance with some embodiments of the invention, the infusion system can further include a heater positioned between the inflatable bladder and the fluid bag, wherein the heater is connected to and controlled by the controller to warm fluid in the fluid bag.

In accordance with some embodiments of the invention, the infusion system can further include a heat sensor in contact with the fluid bag and configured to produce temperature signals representative of the measured temperature of the fluid in the fluid bag and transmit the temperature signals to the controller.

In accordance with some embodiments of the invention, the infusion system can be configured such that the controller configures the display to show the temperature of the fluid in the fluid bag and controls the heater as a function of the measured temperature of the fluid in the fluid bag and a predefined temperature set by a user.

In accordance with some embodiments of the invention, the infusion system can further include a vacuum pump connected to a vacuum port and configured to produce a predefine vacuum pressure (e.g., up to 400 mm Hg or more) at the vacuum port and a suction tube set connected between the vacuum port and a collection reservoir and between the collection reservoir and the surgical tool to draw waste fluid from a surgical site.

In accordance with some embodiments of the invention, the infusion system can further include an inflow fluid flow sensor coupled to the tube set to measure a volume of fluid flowing from the fluid bag to the tool and transmit signals representative of the measured fluid volume to the controller and an outflow fluid flow sensor couple to the suction tube set to measure a volume of waste fluid flowing from the tool to the collection reservoir and transmit signals representative of the measured wasted fluid volume to the controller.

In accordance with some embodiments of the invention, the infusion system can further include a surgical drape configured to collect fluid leaking from the surgical site and wherein the suction tube set is connected between a collection point of the surgical drape and the collection reservoir to draw was fluid from the collection point into the collection reservoir. In addition, the controller can be configured to determine a measure of fluid loss as a function of the received signals representative of the measured fluid volume and the received signals representative of the measured waste fluid volume and configures the display to show the measure of fluid loss on the display.

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

DETAILED DESCRIPTION OF SOME EMBODIMENTS

The present invention is directed to fluid infusion systems that can be used in surgical procedures to supply irrigation fluid and/or distention fluid to a surgical site. In addition, the fluid infusion system can also include provide a vacuum source that can be used remove the fluid and other surgical waste from the surgical site. The system according to the invention is small and light weight enabling it to be used in various surgical settings including a surgical suite, a clinic and a doctor's office.

Figure 1:
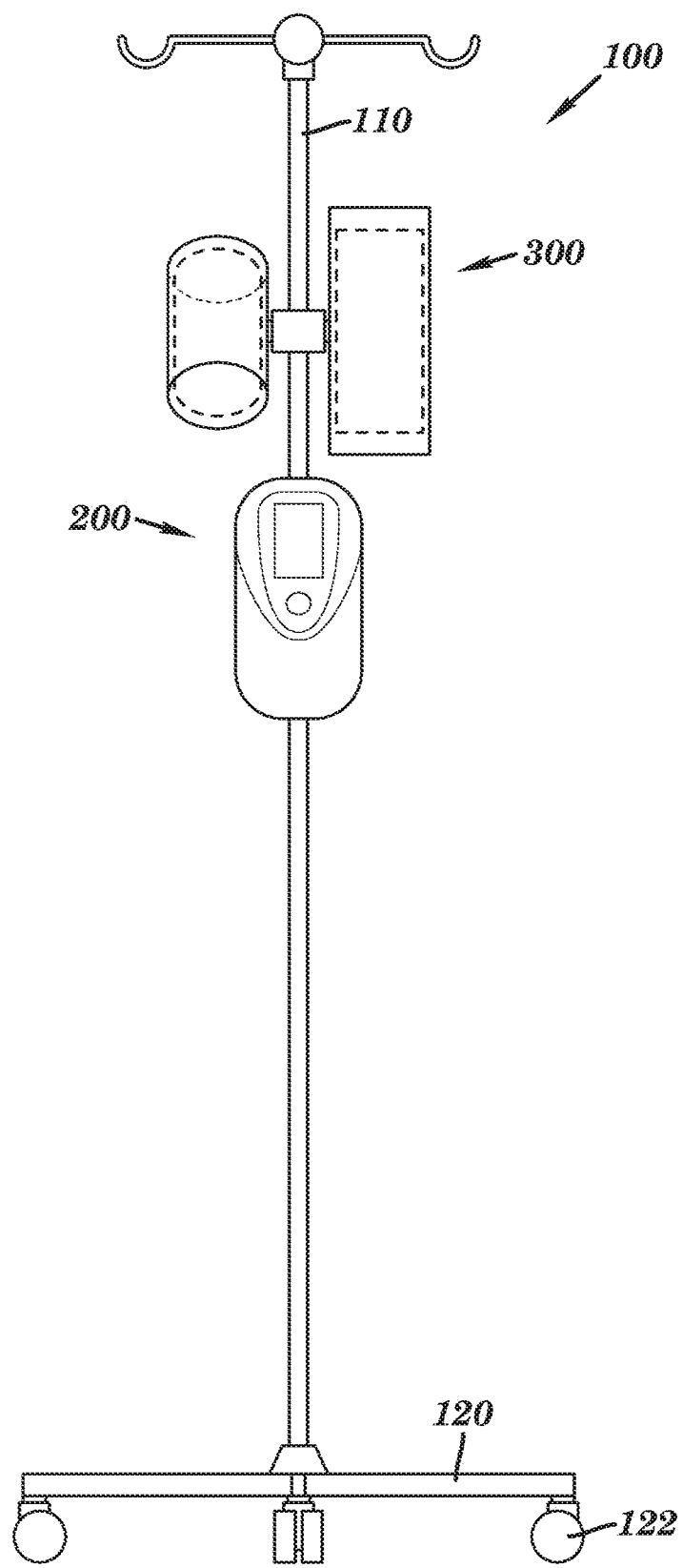
FIG. 1 is a diagrammatic view of an infusion system according to an embodiment of the present invention.
Figure 2:
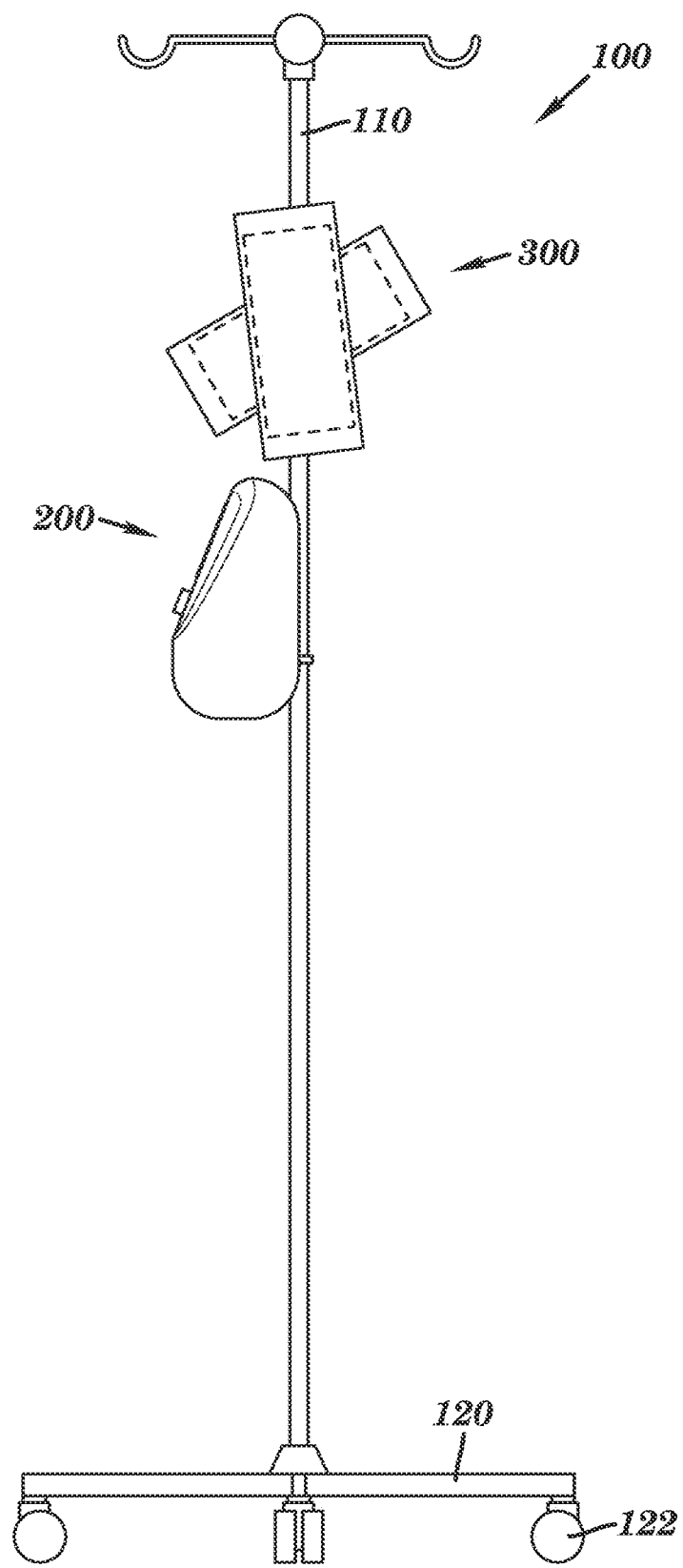
FIG. 2 is a diagrammatic view of an infusion system of FIG. 1 showing the chamber pivot.
Figure 3:
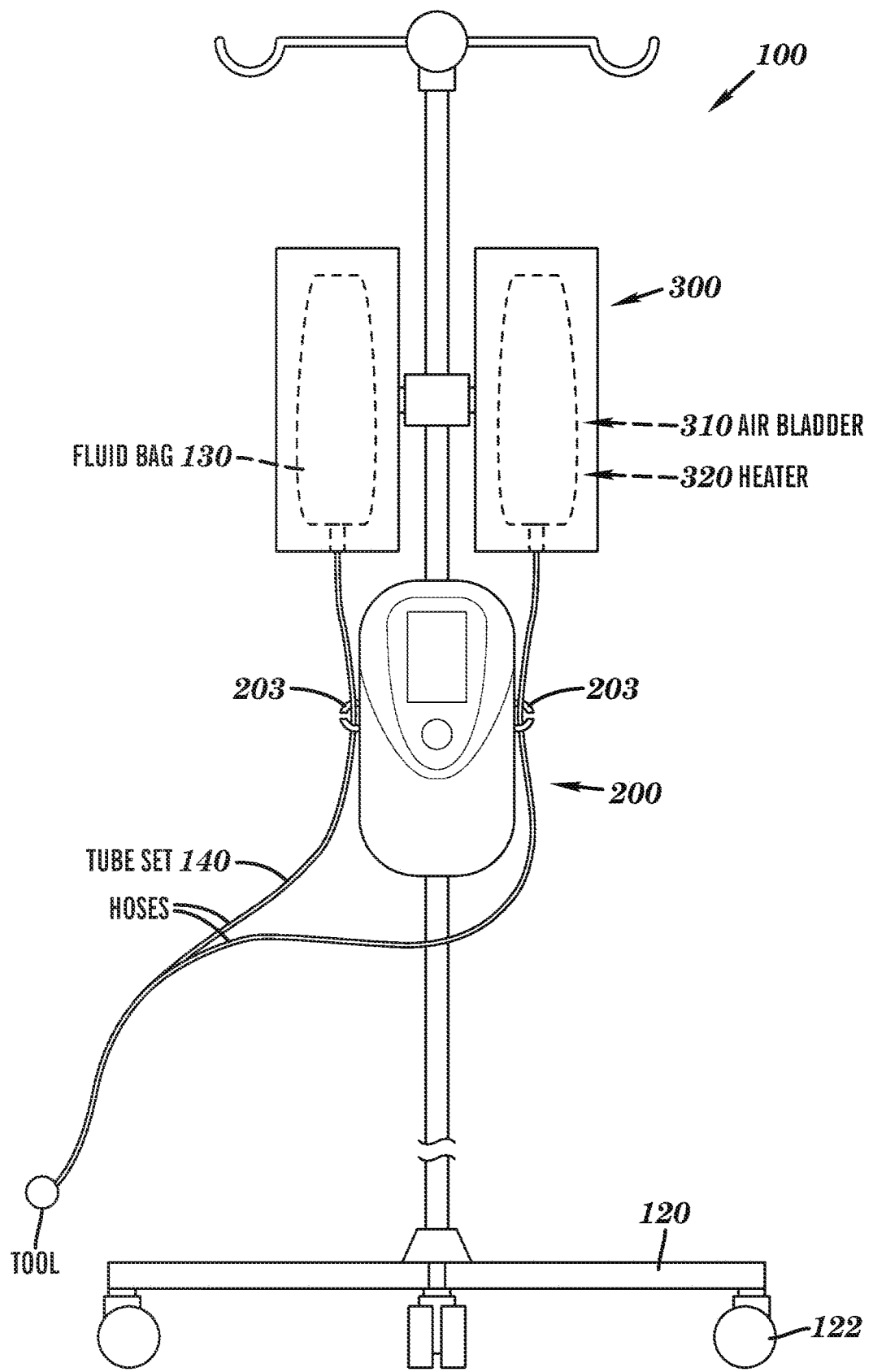
FIG. 3 is a diagrammatic view of the infusion system of FIG. 1 with hoses.

In accordance with some embodiments of the invention, as shown in FIGS. 1, 2 and 3. In accordance with some embodiments of the invention, the system 100 can include a pump assembly 200 and one or more fluid bag chambers 300 (e.g., for supporting saline or other surgical fluids) mounted on an IV pole 110. The fluid bag chamber 300 can house the fluid bag 130 (e.g., saline or other surgical fluids such as irrigation fluid and/or distention fluid), an air bladder 310 to apply pressure on the fluid bag, and a heater 320 to warm the fluid in the fluid bag 130. The fluid bag 130 can be removable and replaceable. The air bladder 310 can be permanently or removably mounted inside the fluid bag chamber 300 and configured to press against the fluid bag 130 inside the chamber (e.g., compress the fluid bag against a wall of the chamber). The heater 330 can be mounted to the air bladder 320 such that it is between the air bladder 320 and the fluid bag 130 and is in direct contact with the fluid bag 130. The heater 330 can be configured to generate heat that is transferred to the fluid in the fluid bag 130 and raise the temperature of the fluid in the fluid bag 130.

The pump assembly 200 can be attached to and supported near the fluid bag chamber 300, for example, mounted to the IV pole 110. In accordance with some embodiments, the pump assembly 200 can be positioned below the fluid bag chambers 300 and the fluid hoses 140 from the fluid bags 120 in the chambers 300 can extend along and be positioned (e.g., by gravity or clips 203) adjacent to the pump assembly 200. While the embodiments of the invention are described in the context of the fluid bag chamber 300 and the pump assembly 200 being mounted to an IV pole 110, the fluid bag chambers 300 and the pump assembly 200 can be mounted to any support structure, such as a wall, a work station or a table.

In accordance with some embodiments, the pump assembly 200 can be adjustably mounted to a support structure (e.g. an IV pole 110) such that its height can be adjusted using a releasable clamp that clamps on the support structure (e.g., a rod or pole) and can be moved up and down in order to accommodate different heights for convenient viewing of the display and to provide the user with ergonomic access to the controls, for example, during a surgical procedure. The IV Pole 110 or other support structure can include wheels 122 at the base 120 to enable it to be repositioned adjacent the patient.

Figure 4:
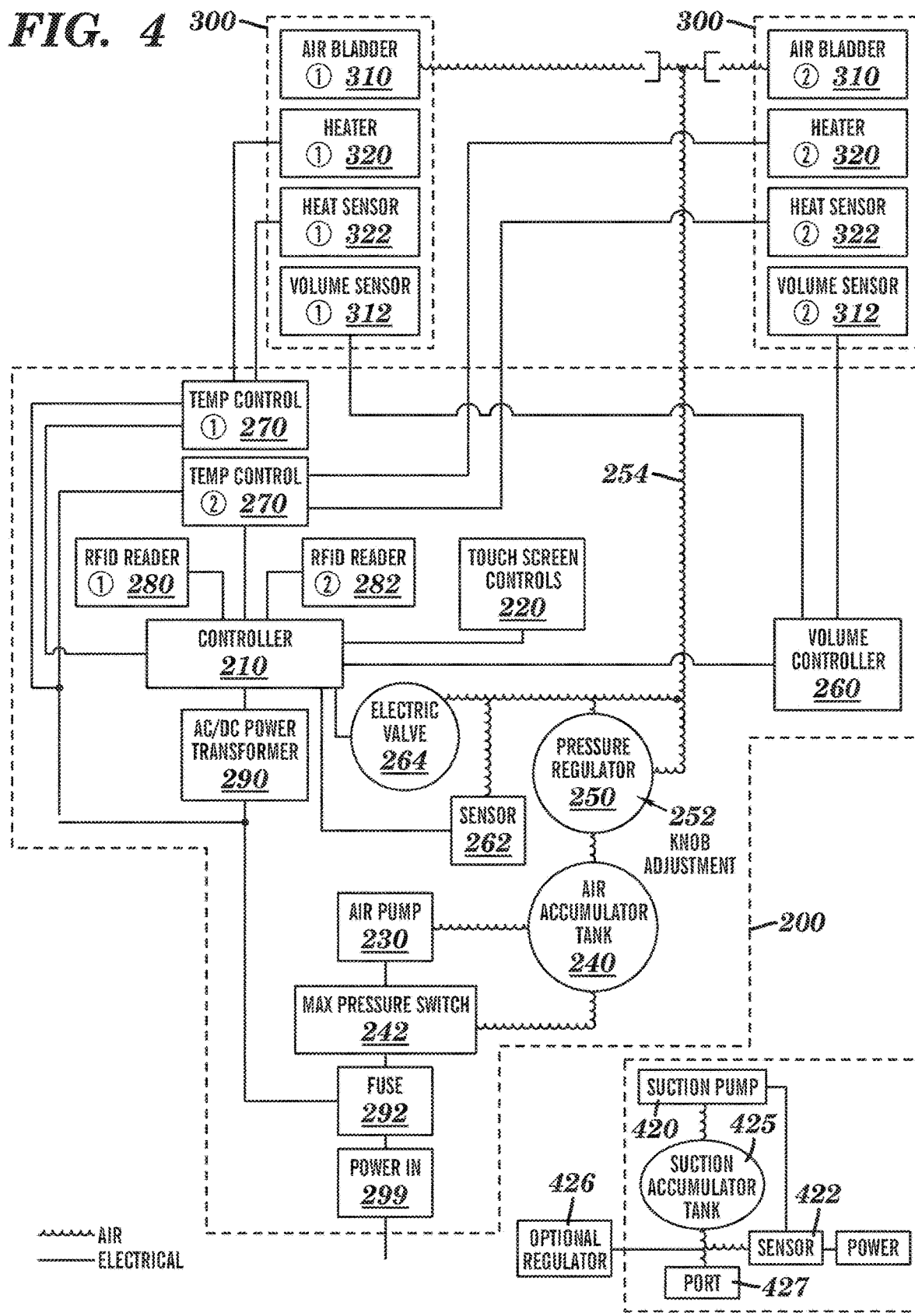
FIG. 4 is a block diagram of the infusion system according to an embodiment of the present invention.

In accordance with some embodiments of the invention, the pump assembly 200, as shown in FIG. 4, can include a controller 210, a touch screen display 220, an air pump 230, one or more accumulator tanks 240, a pressure regulator 250 (including a rotary dial or knob 252), one or more Radio Frequency Identification (RFID), Near Field Communication (NFC) and/or barcode readers 280, emergency stop switch, one or more power supplies 290 (e.g., AC and/or DC), pressure switch 242, and a variety of mechanical interlock switches and safeties that are wired to the controller 210 in such a way that the pump 230 will only operate if the conditions are favorable.

In accordance with some embodiments, the pressurized air runs through hoses 254 from the pump assembly 200, through or adjacent to the IV pole 110 through detachable connectors 256 and 304 to the air bladders 310 in the fluid bag chambers 300. In accordance with some embodiments of the invention, the fluid bag chambers 300 can include a heater 320 that is connected by wires to the controller 210 to enable the controller 210 to control the heater 320 to warm the fluid in the fluid bag 130. Optionally, a temperature control element 290 including for example, power transistors and other components to control the supply power to the heating element in the heater 320 can be connected between the controller 210 and the heater 320.

Existing prior art systems typically use peristaltic pumps or other types of pumps that tend to cause the fluid flow to pulsate which can cause erratic movement of tissue in the surgical site during an operation. In accordance with some embodiments of the invention, the pump assembly 200 can include an air pump 230 that produces compressed or pressurized air that is stored in one or more accumulator tanks 240. The compressed air can be used to inflate the air bladders 310 that apply pressure on the fluid bags 130 to push the fluid through the supply tubing 140 of system to the surgical tool 150 (e.g., an endoscope) that can be inserted into the patient at the surgical site. In accordance with some embodiments of the invention, the compressed air can be produced by a quiet air pump 230 inside the pump assembly housing 202 that is capable of producing at least 5-20 psi, depending on the procedure and tools used. Alternatively, the air pump 230 can be remotely located, such as in the base of the IV pole 110 or away from the surgical suite or operating room (e.g., the air compressor that is part of the building infrastructure). The accumulator tanks 240 can be sized to accommodate the necessary volume and pressure of air to deliver fluid as needed during a given procedure without the need to turn on the pump 230 or connect the accumulator tank to an external source. In some embodiments, an air hose can connect the pump assembly 200 to the compressed air connection on the wall of the facility and a valve connected to the controller 210 (and optionally, a pressure regulator) can be provided in the pump assembly 200 to connect the compressed air to the accumulator tank 240.

In accordance with some embodiments, the compressed air can be sent to and stored in one or more accumulator tanks 240 in the pump assembly 200, the base of the IV pole 110 or in any location adjacent the surgical suite. The accumulator tank 240 acts as a buffer to reduce or prevent the pulsating flow produced by the pump 230 from causing the delivery of fluid to pulsate. This enables the air bladder 310 to apply stable, non-pulsating pressure on the fluid in the fluid bag and provides for stable (e.g., non-pulsating) and consistent delivery of the fluid to the surgical site. It also provides for rapid response (e.g., no lag or delay waiting for the pump to build pressure) and allows the pressure to be controlled by a downstream adjustable regulator 250.

In accordance with some embodiments of the invention, the system 100 can include one or more accumulator tanks 240 and the size of the accumulator tank 240 can be selected to provide a predefined volume and pressure to the air bladder 310 to enable the fluid to flow for a predefined amount time or fluid volume. For example, the accumulator tank 240 volume can be configured or selected to hold enough compressed air to drain two or more full fluid bags and/or to last for the entire length of the surgical procedure in which the fluid is used, without the need to operate the pump that can cause noise and fluid pulsation during the surgical procedure. In accordance with some embodiments of the invention, two or more accumulator tanks 240 can be used, connected in series or in parallel between the air pump and the air bladders 310, to enable a predefined volume of air to be stored for the entire duration of a desired surgical procedure.

In accordance with some embodiments of the invention, the accumulator tank 240 can hold a ½ liter of air at maximum pressure of 10-30 psi or more, to provide sufficient air volume to maintain the fluid pressure with a desired optimal flow rate. The accumulator tank 240 can be incorporated into the molded pump housing. Alternatively the accumulator tank can be a sealed cylinder that forms part of or is incorporated into the IV pole and provides multiple connection ports along the length of the IV pole.

The volume and pressure for a given system 100 can be determined using Boyle's Law (e.g., $P1 V1 = P2 V2$) for ideal gases. For example, a typical saline (e.g., irrigation or distention fluid) bag holds 1 liter of fluid and the maximum needed pressure to deliver the fluid can be, for example, 5 PSI. If it is assumed that 2 bags of saline will be used during the procedure, the pump and the accumulator tanks can be selected to provide the necessary performance. For example, the pump 230 and accumulator tank 240 can be selected to have a max pressure of 20 PSI and the tank can have a volume of at least 0.5 liters. Alternatively, the system can be configured with a 1 liter accumulator tank and a 10 psi pump.

In accordance with some embodiments, the air pump 240 can be a small, self-venting diaphragm pump to ensure that the maximum set pressure cannot be exceeded. The air pump 240 can be configured to run when the Start button on the display 220 is pressed and only if a cut-off pressure switch is not triggered (e.g., the pressure inside the accumulator tank is below a predefined threshold). The system 100 can include a pump pressure control circuit that includes an electrical pressure switch 242 that is connected to air accumulator tank 240 can controls the electric power to the air pump 230. The electric pressure switch 242 can be configured to remove power to the pump 230 if a pressure threshold or maximum pressure (e.g., approximately 20 psi) is sensed in the accumulator tank 240. As air is drawn out of the air accumulator tank 240 into the air bladders 310, the pressure in the accumulator tank drops below the maximum pressure causing the power to the pump 230 to be turned back on until the pressure returns to the maximum pressure. As a person having ordinary skill in the art will appreciate, the maximum pressure will vary with the configuration of the system 100 according to the invention, including the size and safe maximum pressure of the accumulator tank, as well as the size of the fluid bag, the flow properties of the surgical tool (e.g., the fluid channel of the endoscope) and the diameter and maximum safe operating pressure of the tubing 140 connecting the fluid bag 130 to the surgical tool 150.

In accordance with some embodiments of the invention, the pressurized air from the accumulator tank 240 flows through tubing to a pressure regulator 250 that maintains the air pressure to the air bladders 310—the air pressure can be set by the operator. In accordance with some embodiments the pressure regulator 250 can include a mechanically controlled pressure regulator that enables the user to set the pressure by turning a knob or dial 252 mechanically coupled to the pressure regulator 250. The regulator 250 can be housed inside the pump assembly 200 with the regulator control knob 252 extending from the pump assembly housing. The position of the pump assembly 200 can be adjusted along the IV pole such that the position of the regulator control knob 252 can be positioned for easy access by the operator (e.g., without the need to stand up). In accordance with some embodiments of the invention, the pressure regulator 250 can include an electronically controlled pressure regulator that is electrically connected to the controller 210. The controller 201 can figure the display 220 to provide up/down or +/− button icons on the display screen to enable the user to control the pressure (e.g., when the user presses the button icons, the controller 210 sends the appropriate signal to the pressure regulator to change the set point pressure. Alternatively, a control knob potentiometer can be used to provide an analog input to the controller 210 to control the electronic pressure regulator.

Figure 7:
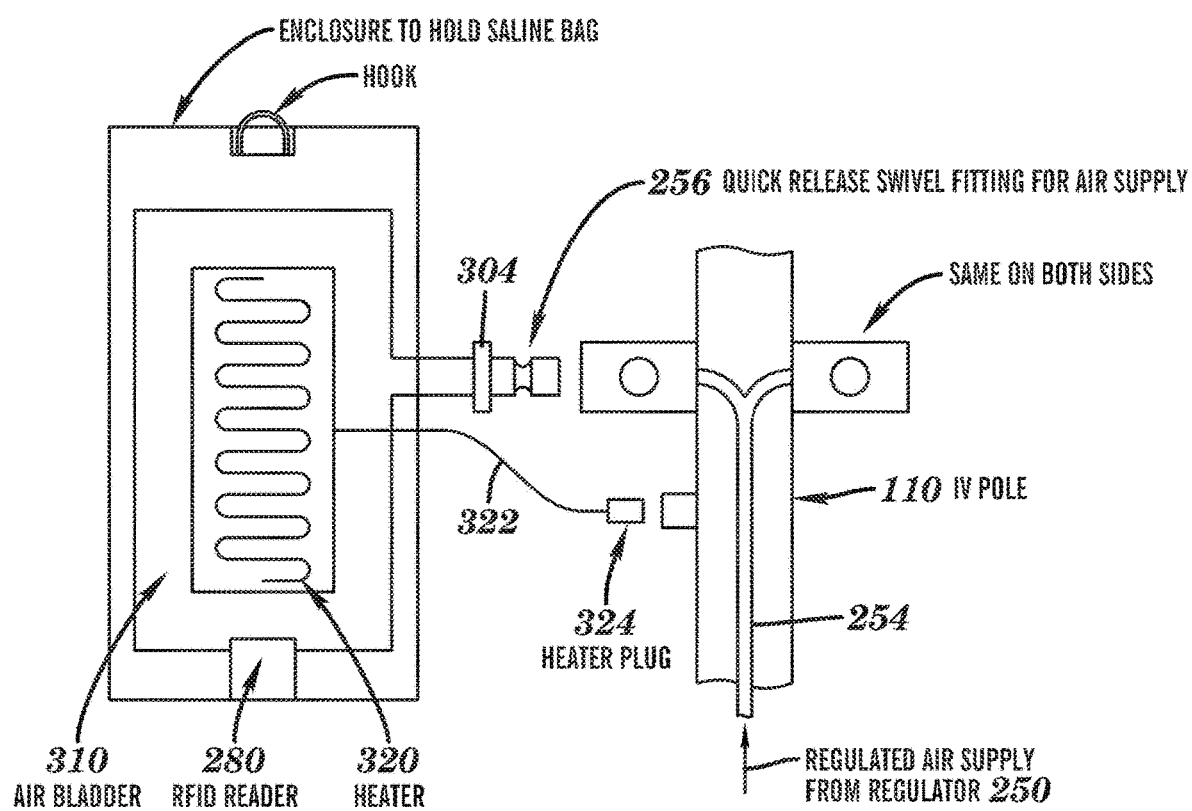
FIG. 7 is a detail view of the chamber attachment.

In accordance with some embodiments of the invention, as shown in FIG. 7, the pressurized air can be routed to the air bladders 310 in the fluid bag chambers 300 through detachable fluid connectors 256 and 304 that can also be used to attach the fluid bag chambers 300 to the IV pole 110 (or other support structure). The detachable fluid connector can be constructed using a quick connect air fitting that includes a male component 304 that fits into a female component 256 with a sliding sleeve that opens and closes the female component to lock the two components together forming an air tight seal. The fluid connectors can allow the fluid bag chambers to be quickly removed as well as allow the fluid bag chamber to be rotated to facilitate removal and installation of the fluid bags 130. The quick connectors can be installed into a socket to provide additional support when swiveled. Alternatively, a separate swivel component can be used to connect the fluid bag chamber to the IV pole and a separate tube with detachable connection can be used to connect the air accumulator tank 240 to the air bladder 310. Standard push-to-connect air fittings can be used to provide detachable air connections.

The detachable connector 256, 304 permits the fluid bag chamber 310 to pivot on a horizontal axis so that the fluid bag 130 can be inverted such that the base of the bag 130 is above the top of the bag 130. In use, the filled fluid bag 130 can be hung on a hook 306 inside the fluid bag chamber 310 (with the air bladder compressed) and then the fluid bag chamber 300 can be pivoted so the filled fluid bag 130 is inverted while the user spikes the fluid bag 130 (e.g., connects the fluid delivery tubing to the fluid bag). This enables the fluid bag 130 to be connected to the tubing 140 without experiencing the common problem of fluid dripping from the bag 130 when it is spiked. In accordance with some embodiments, the fluid bag chambers 300 can also include a hinge enabling them to be opened to insert and remove the fluid bag as well for priming of the pump (or filling the accumulator tank to maximum pressure) when the enclosure is open and closed. In accordance with some embodiments of the invention, a sensor can be installed on the cover so the air pump is only activated when the lid is closed. In accordance with some embodiments of the invention, a spiking mechanism can be incorporated into the fluid bag chamber that allows the distention fluid container to be directly coupled to the inflow tubing without the need to manually spike the fluid bag or container. Alternatively, the air pump 230 can be automatically or manually shut off and/or the air bladder 310 deflated when the chamber 300 is open. This can be done by either a manual or electrical valve 254 diverting the air pressure to one of 3 different locations: the atmosphere (e.g., venting), sealing it off (e.g., closing the connection 258 between the air accumulator tank 240 and the air bladder 310 in order to fill the accumulator tank), or flow into the airbladder (during operation/run mode). The connection 258 can also include a pressure sensor 252 that measures the pressure in the connection 258 and sends the pressure information to controller 210. The controller 210 can monitor the pressure in the connection 258 and compare it with upper and lower limits to signal alarms (e.g., pressure low alarm or pressure high alarm) or change the position of the valve 254 if a condition (e.g., the pressure is over the safe limit).

In accordance with some embodiments, the fluid bag chambers 300 can be molded enclosures that are available in different sizes to match a variety of sizes of fluid bags 130. For example, fluid bag chambers 300 can be sized to accommodate standard 500 ml, 1000 ml, 2000 ml, and 3000 ml (as well as custom sized) fluid bags 130. In accordance with some embodiments, the fluid bag chambers 300 can be shaped to accommodate the blow-fill-seal containers (e.g., available from Asept Pak Inc in Malone, N.Y.) that are becoming increasing popular for IV fluids as an alternative to the standard fluid bags.

Figure 8:
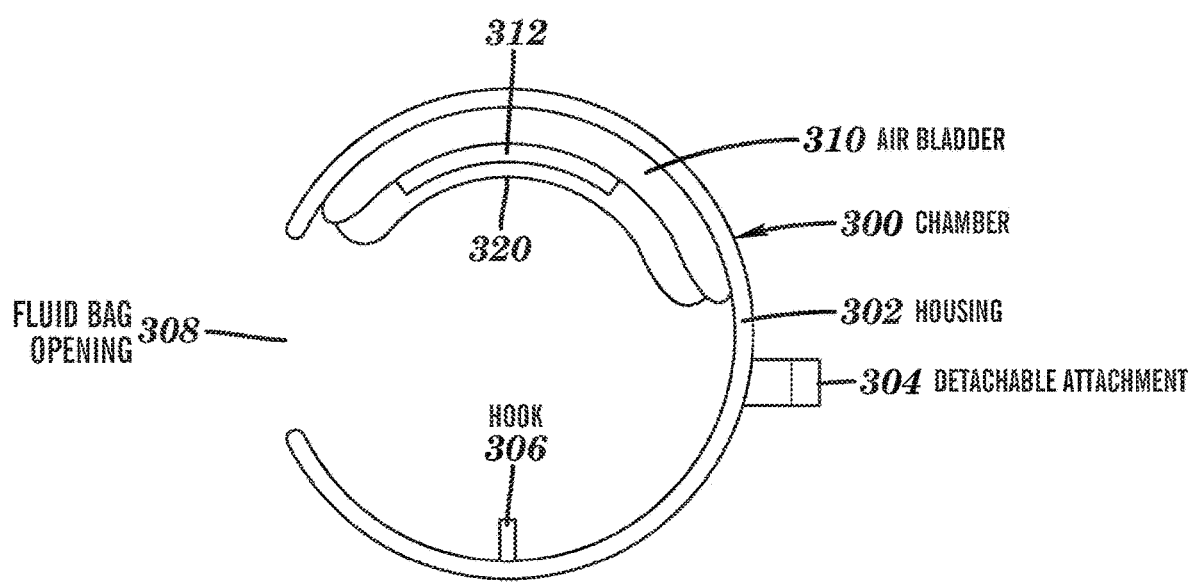
FIG. 8 is a top view of a chamber.

As shown in FIGS. 4 and 7-10, the fluid bag chamber 300 according to some embodiments of the invention can include an inflatable air bladder 310, a heater 320, a temperature or heat sensor 322, and a volume measuring sensor 312. In accordance with some embodiments, as shown in FIG. 8 the fluid bag chamber 300 can be round or have any tubular shape and optionally include a side opening (e.g., in addition to a hinge or as an alternative to the hinge) to allow a fluid bag to be easily inserted or removed. For example, the fluid bag chamber 300 can have a C or U shaped cross-section. The fluid bag 130 can be inserted into the side, top or bottom opening and hung on a hook 302 at the top of the fluid bag chamber 300 to keep it from falling or collapsing. The bottom of the chamber can be at least partially open to provide access to the base of the fluid bag 130 so that the bag can be spiked (e.g., connected to delivery tubing).

The fluid bag chamber 300 according to the invention provides several improvements over the prior art. The C-shaped chamber allows for ease of access for inserting and removing fluid bags or other containers. The pivoting fluid bag chamber 300 enables the fluid bags 130 to pivoted to facilitate attachment, enabling the user easy access to the connection port on the fluid bag 130 and permits spiking (e.g., tubing connection) without leaking. The detachable connector 265, 304 can serve several functions—allowing the fluid bag chamber 300 to pivot for ease of use as well as for compact storage (e.g., the fluid bag chamber 300 can be easily removed) and for use in an office environment. Systems according to the present invention allow for flexibility and expansion as larger (or smaller) sized fluid bag chambers 300 can be easily installed. The present invention is not limited to the C shaped fluid bag chambers 300. In accordance with some embodiments of the invention, the fluid bag chamber 300 can be design and configured to accommodate any size and shape fluid bag 130 (e.g., saline bags) that is available now or in the future. This enables the fluid delivery system 100 according to the invention to be adapted for use in a broad range of surgical environments, include traditional surgical suites as well out-patient clinics and doctor's offices. Likewise, this enables the fluid delivery system to be used in a variety of surgical procedures in which a body cavity (e.g., the urinary bladder, bone joints, uterine cavity, etc.) is distended with fluid for an operative endoscopic procedure.

In accordance with some embodiments, the pressured air can be routed via tubing from the pressure regulator 250 to a T junction and the fluid bag chambers can be attached by the detachable connectors on each side of the T (or Y shaped) junction. In accordance with some embodiments, all of the fluid bag chambers 300 can be configured receive the same air pressure, that is, the air pressure to each chamber 300 is not individually adjustable. In accordance with some embodiments, the pressurize air can be routed through the T junction and each fluid bag chamber 300 can include a separate pressure regulator 250, such that each the air pressure in each air bladder 310 is individually adjustable.

During use, the air bladders 310 can be initially empty providing sufficient space in the fluid bag chamber 300 to accommodate a full fluid bag 130. As the air bladder 310 fills, pressure from the air bladder 310 on the fluid bag 130 displaces the fluid from the fluid bag at a constant pressure based on the operators' set point. The pressure regulator 250 serves to maintain the constant pressure in the air bladder and any drop or rise in pressure of the fluid in the fluid bag 130 or the tube set 140 will cause the pressure regulator to increase or drop the air pressure supplied to the air bladder. This enables the system 100 to maintain a substantially constant fluid supply pressure (e.g., for both irrigation and distention purposes) during the entire procedure. The pressure of the dispensed fluid can be determined as a function of the pressure in the air bladder 310 which can be measured by pressure sensor 262 connected between the air pressure regulator 250 and the air bladder 310. In accordance with some embodiments, the pressure of the dispensed fluid can be the same as the pressure in the air bladder 310. Alternatively, depending on the size and configuration of the tubing set 140 as well as the tool 150, the pressure of the dispensed fluid can vary.

After the fluid bag 130 is empty or the procedure is completed, the operator can press a button on the pump assembly 200 housing or the display 220 which releases the pressure (e.g., mechanically or electrically, such as by opening a valve) in and/or to the air bladder 310 to deflate the air bladder 310. After the bladder 310 is deflated, the operator can remove the fluid bag 130 and the tube set 140 for disposal. The chamber 300 is then ready for another fluid bag 130 to be installed.

Figure 9:
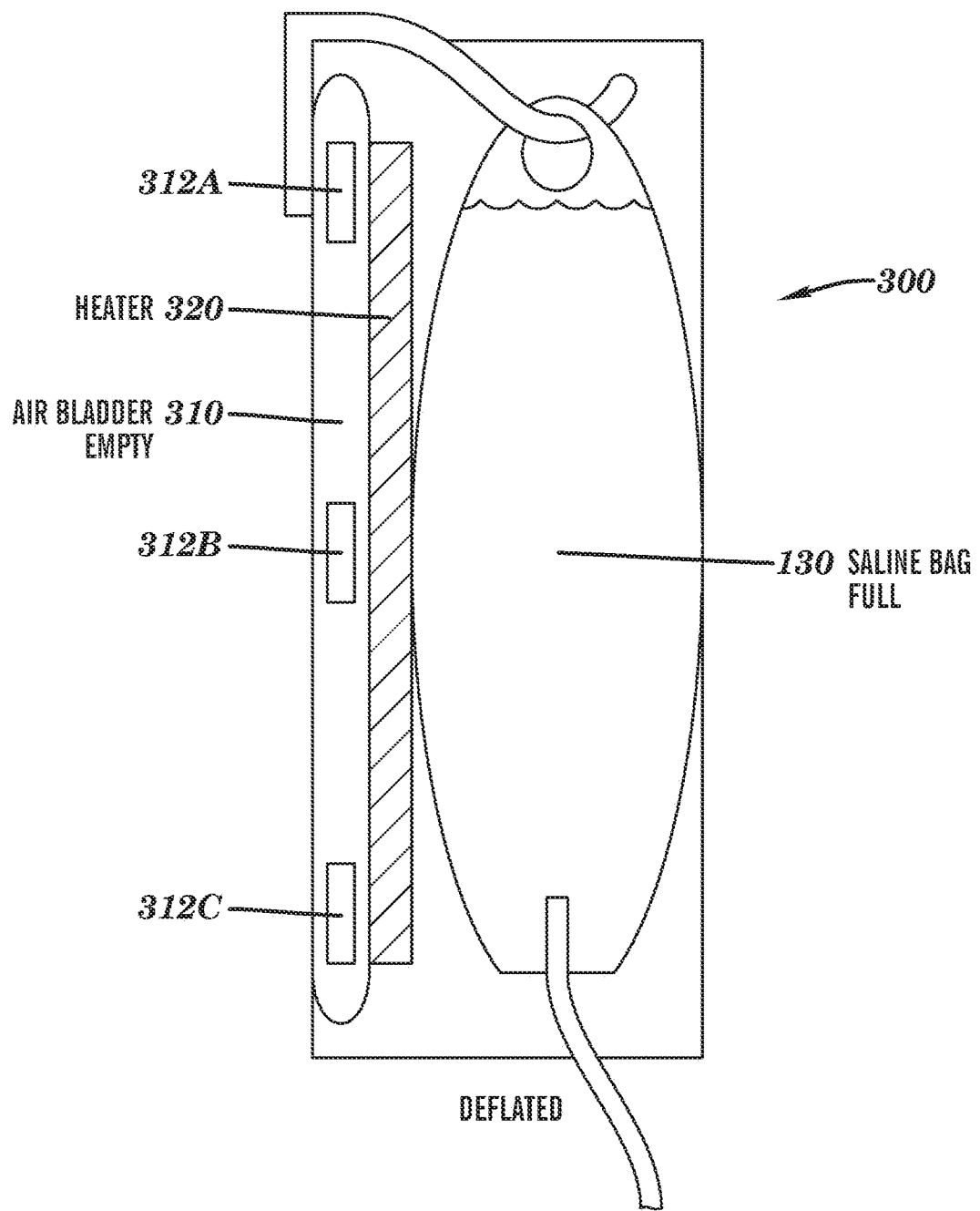
FIG. 9 is a cross-sectional view of the chamber with a full fluid bag.
Figure 10:
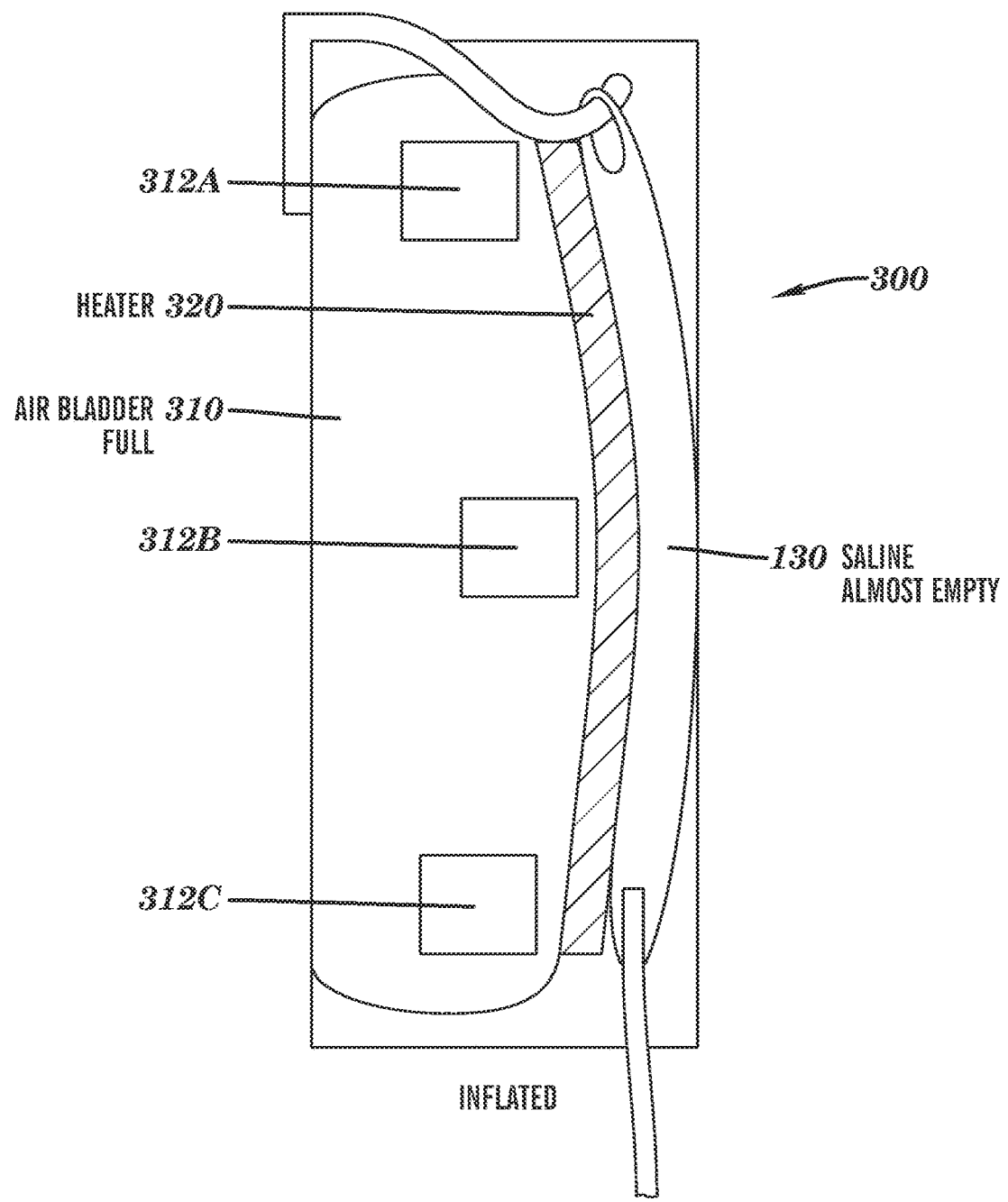
FIG. 10 is a cross-sectional view of the chamber with an empty fluid bag.

The volume of fluid in the fluid bag can be measured in a variety of different ways, for example, by measuring directly or indirectly the thickness (and therefore the volume) of the fluid bag 130 or the air bladder 310. In accordance with some embodiments of the invention, one or more deflection sensors 312 can be located inside the air bladder 310 to determine how much fluid remains in the fluid bag 130. For example, as shown in FIGS. 9 and 10 three deflection gauges can be mounted against the inner surface of the air bladder, at the top 312A, middle 312B and base 312C of the air bladder. The deflection gauges or sensors can be a "Long Flex Sensor" available from adafruit.com (product id: 182)—these sensor change their resistance as the sensor is flexed or bent. For example, a full bag of saline would occupy most of the space inside the fluid chamber causing the air bladder to be concave and the deflection sensors to be concave as well. As the air bladder expands the surface of the bladder will change from concave to convex and the deflection sensors would also become convex and change their resistance. If there is a series of deflection sensors on the surface of the air bladder then the average resistance of the 3 sensors should coincide with the approximate volume of fluid that has been dispensed. The sensors can be calibrated by dispensing predefined volumes of fluid and recording the resistance and the resistance change after each volume is dispensed. These values can be stored in memory of the controller 210 and used to extrapolate the volume from the resistance values or the average of the resistance values. The volume of dispensed fluid and/or the volume of remaining fluid can be displayed on the screen so the operator can monitor the fluid dispensed and/or verify there is an appropriate amount of fluid remaining to complete the procedure. When the system is used with a collection drape and vacuum, the volume of waste fluid can also be measured and transmitted to the controller 210 so that the amount of lost fluid (e.g., such as to intravasation) can be determined (e.g., as function of the difference between the dispensed volume and waste volume) and displayed to the user.

In accordance with some embodiments of the invention, the volume of the fluid bag 130 or the air bladder 310 can determined by measuring the distance through the fluid bag 130 or the air bladder 310. The distance could be used to calculate or extrapolate a given volume based on the minimum and maximum distance range measured between a full air bladder 310 (e.g., empty saline bag) and empty air bladder 310 (e.g., full saline bag). In accordance with some embodiments of the invention, the distance can be measured using one or more ultrasonic sensors that use the change in sound signals that pass through (e.g., using a transmitter on one side and a receiver on the other side of) or the fluid bag 130 or the air bladder 310. In accordance with some embodiments of the invention, the distance can be measured using one or more ultrasonic sensors that use the change in sound signals that pass through and are reflected back (e.g., using a transmitter and receiver on the same side of) or the fluid bag or the air bladder. As the thickness of the fluid bag 130 changes, the received sound signals change a function the thickness (e.g., the received signal attenuation or amplitude as compared to the transmitted signal can change). In accordance with some embodiments of the invention, the distance can be measured using one or more optical (e.g., infrared or visible light) sensors that use the change in optical signals that pass through (e.g., using a transmitter on one side and a receiver on the other side of) or the fluid bag or the air bladder. In accordance with some embodiments of the invention, the distance can be measured using one or more optical (e.g., infrared or visible light) sensors that use the change in optical signals that pass through and are reflected back (e.g., using a transmitter and receiver on the same side of) or the fluid bag or the air bladder 310. As the thickness of the fluid bag changes, the optical signals change a function the thickness (e.g., the received signal attenuation or amplitude as compared to the transmitted signal can change). The volume values can be displayed on the screen so the operator can verify there is an appropriate amount of fluid remaining.

In accordance with some embodiments, an array of sensors can be used to measure fluid volume. The volume can be determined as a function of an average of two or more sensors or a single sensor can be used to measure volume. When electrical sensors are used, an electrical connection can be used to provide power and to send signals back to the controller 210. The signals can be used to calculate the fluid bag 130 volume and then presented a graphical or numerical representation on the touch screen display showing the volume of fluid used or remaining in the bag.

In accordance with some embodiments, the tube set 140 can include a fluid volume sensor that reports the volume of fluid flowing past the volume sensor to the controller 210. The sensor and the tube set 140 can be disposable. In accordance with some embodiments, the volume sensor can include a magnetically coupled impellor that coupled to a sensor that is part of the pump assembly or the fluid bag chamber that reports fluid flow through the tube set 140 to the controller 210. In accordance with some embodiments, the volume sensor can include an ultrasonic sensor that is part of the pump assembly or the fluid bag chamber that reports fluid flow through the tube set 140 to the controller 210.

In accordance with some embodiments of the invention, the fluid bag chamber 300 can include a heater 320 positioned to be in contact with the fluid bag 130 installed in the chamber 300. In accordance with some embodiments of the invention, the heating element 320 can be positioned between the air bladder 310 and fluid bag 130 such that the heater 320 is being pressed against the fluid bag 130 by air bladder 310 during used. In accordance with some embodiments of the invention, the heater 320 can be positioned between the wall of the fluid bag chamber 300 and fluid bag 130. In accordance with some embodiments, the heater 320 can include a low power heating element that is not intended to raise the fluid to the desired temperature, but only to maintain the temperature of the fluid as it is expected that the fluid will be raised to the desired temperature prior to installing the fluid bag 130 in the chamber 300. In accordance with some embodiments, the heater 320 can include a higher power heating element that can be used to raise the fluid to any desired temperature.

In accordance with some embodiments, the heater 320 can include one or more heating elements 322, for example, a 3"×10", 200-watt silicone heating element (available from Keenovo (Shanghai, China) or a similar supplier). The heating element 322 can be mounted to the surface of the air bladder 310 or the inner surface of the fluid bag chamber 300 such that the heater 320 is in direct contact with the fluid bag 130. In accordance with some embodiments of the invention, the heater can include an infrared heater, passing the fluid through a disposable heated tray or manifold, and/or wrapping the fluid hose around a headed cylinder several times to increase the dwell time. In accordance with some embodiments, a temperature sensor 322 near the base of the bag 130 (away from the heating element) or on the tubing 140 connected to the bag 130, can be used to read to actual temperature of the fluid. In accordance with some embodiments of the invention, the temperature of the fluid from each chamber 300 can be adjusted separately, that is, each chamber can have a different fluid temperature setting.

In accordance with some embodiments of the invention, the fluid bag chamber 300 can include a variety of electrical connections to the electronic components in the chamber 300. The fluid bag chamber 300 can include the following electric components: one or more electric heaters, one or more volume measurement sensors, and one or more temperature sensors. These electric components can by connected to the controller 210 by wires through a separate connector fitting for each sensor or all the connection can share the same connector fitting. These connectors allow the wires to be easily disconnected and reconnected when swapping out chambers 300. For example, in some embodiments of the invention, the connector can be an 8 pin DIN connector that can be easily disconnected and reconnected when the air chamber is swapped. In accordance with some embodiments of the invention, the connector does not pivot with the air connection and the wire provides sufficient slack to enable pivoting. In accordance with some embodiments of the invention, the connector can pivot as part of the air connection, for example, by being arranged around the pivot axis of the air connector. For example, the connector can include a rotary union that has both electrical and pneumatic connections inside, such as a Deublin (Waukegan, Ill.) part number 1102-070-082. The rotary union enables quick connection because of the dual nature of the coupled pneumatic/electrical contacts.

Figure 12:
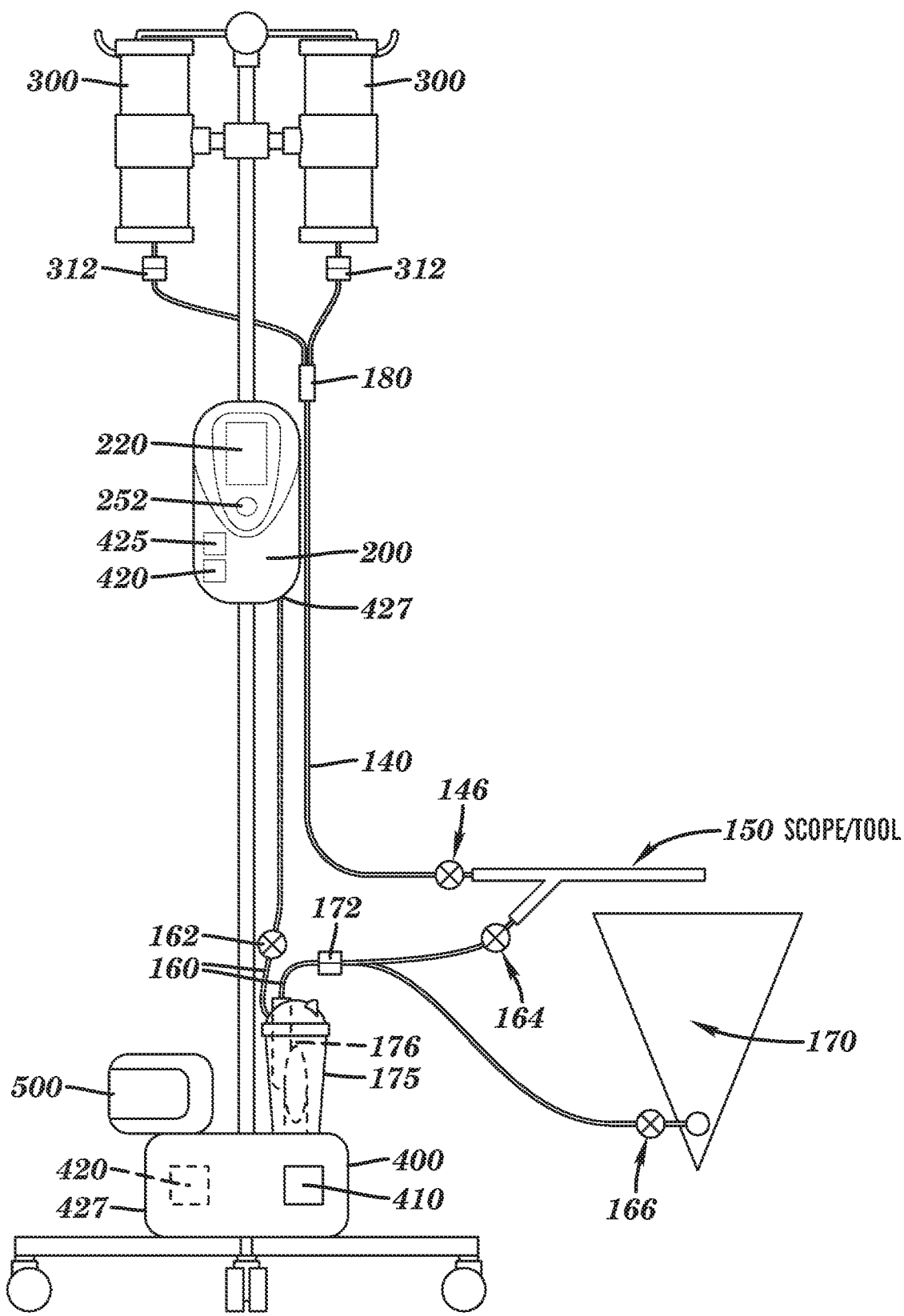
FIG. 12 is a diagrammatic view of an infusion system according to an embodiment of the present invention.

In accordance with some embodiments of the invention, the system can include a fluid bag pre-heater 500 as shown in FIG. 12. The fluid bag pre-heater 500 can include a housing 502 and a heating element 520 (e.g., a 3"×10" or larger, 200-watt silicone heating element available from Keenovo, Shanghai, China or a similar supplier) set at a preset temperature. Unheated bags (at room temperature) can be placed in the pre-heater 500 pre-heating, enabling the fluid (e.g., saline) to get up to a preset temperature (e.g., 98 degrees) more quickly in anticipation of placing the bag into the fluid bag chamber 300. The fluid bag pre-heater can located in or on the base of the IV pole 110. The location of the preheater 500 will lower the center of gravity of the system 100 and also allow for the operator to quickly swap out the saline bag 130 if needed. The pre-heater 500 can be connected the system battery, a separate battery or configured such that it will only work when it is plugged into an AC power outlet.

In accordance with some embodiments of the invention, the system can include a battery 410 and battery charging circuitry 412. The battery 410 and charging circuitry 412 can be contained in a metal or plastic housing 400 that is mounted at or in the base of the IV pole 110. The size of the battery 410 can be selected to allow the unit to be used for a predetermined period of time (e.g., the expected length of a surgical procedure, with some margin of safety) so that it can be moved freely around the room (the operating room, surgical suite or office) without the need to be tethered to an AC power outlet. The battery housing 400 can include a circuit with a display that can display the status of the battery including the time remaining. In accordance with some embodiments of the invention, the battery 410 can be selected to enable the system to remain fully operational during procedures that are typically of short duration, for example, the battery can be sized (e.g., 10 Ah) to run the system for approximately 30 minutes at 250 mmHg (e.g., approx. 5 psi).

The touch screen display 220 can be controlled by the controller 210 to present a Graphical User Interface (GUI) that enables the user to control the operation of the system 100 by touching icons and controls presented on the display 220. The touch screen display 220 can include a resistive or capacitive surface that records the location of the contact with screen and is programmed to perform a function which can change the way the controller 210 and the system 100 operates. A resistive screen is preferred since operators will typically have gloves. Alternatively, mechanical buttons and switches can be provided to control the operation of the system with or without a touch sensitive screen. The screen 220 can display the fluid temperature and fluid pressure. A pressure "dial" or other icon (e.g., up/down buttons or +/− buttons) can be presented on the screen 220 to enable the user to easily adjust the fluid pressure. A temperature "dial" or other icon (e.g., up/down buttons or +/− buttons) can be presented to the user to enable the user to easily adjust the fluid temperature. After the tubing set 140 is selected and installed, the operator can set the system 100 to the desired or recommended pressure and temperature within the limits set by the installed tubing set 140.

Figure 11:
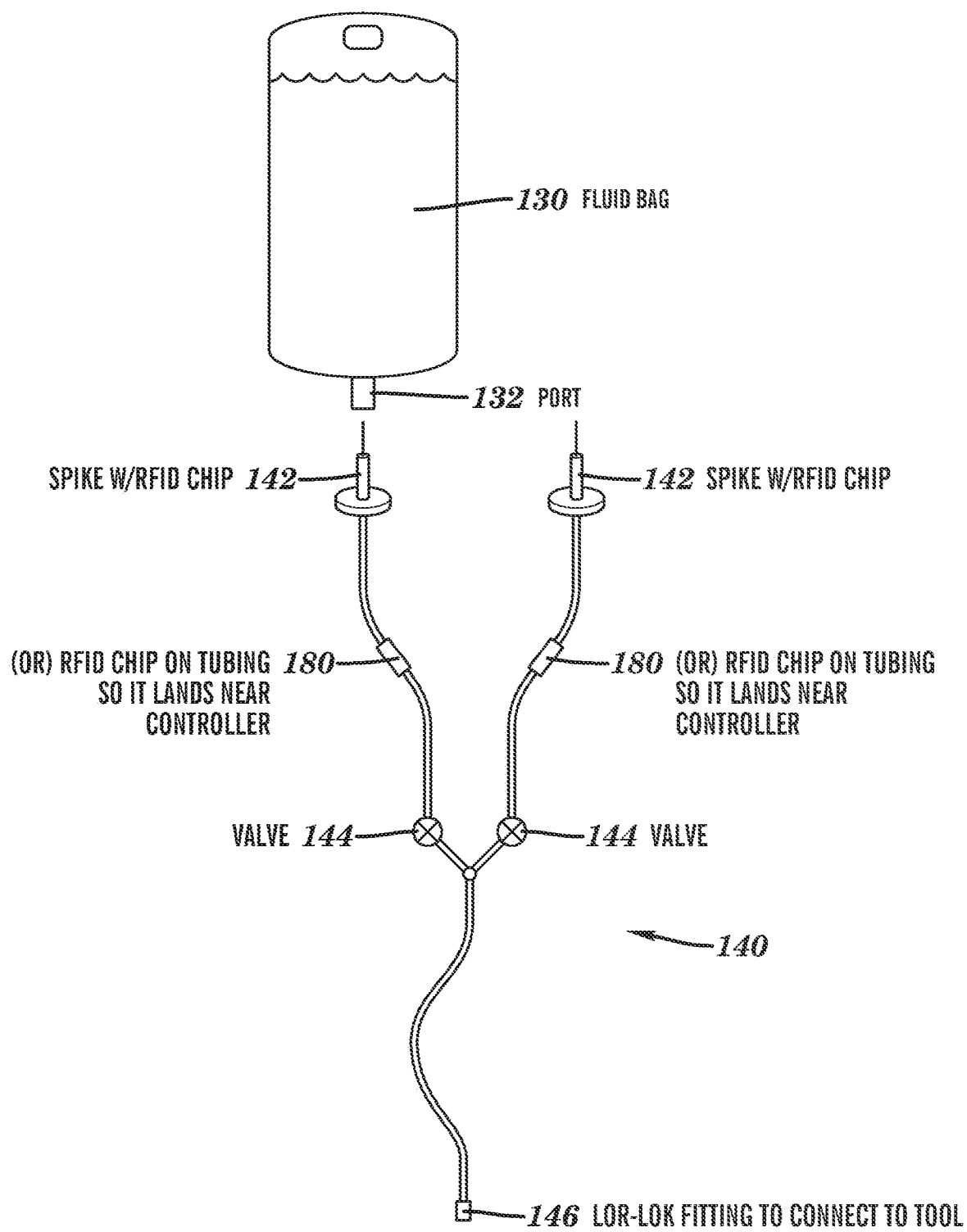
FIG. 11 is a diagram of the fluid bag and hoses.

In accordance with some embodiments of the invention, as shown in FIG. 11, the tubing set 140 can include a length of tubing selected because its physical characteristics make it suitable for a particular procedure. The tubing set 140 can include at the proximal end, one or more spike ends 142 for connecting the tubing set 140 to a fluid bag 130. The tubing set 140 can include one or more RFID, NFC, and/or barcode tags 180, one or more valves 144 and at the distal end, a fitting (e.g., a Luer Lok™ fitting) for connecting the distal end to the tool 150. In accordance with some embodiments, the proximal end can be bifurcated or split into two or more branches to enable the tube set 140 to be connected to two or more fluid bags 130.

In accordance with some embodiments of the invention, each tube set 140 can include one or more RFID/NFC tag (or a barcode label) 180 that can be read by a reader 280 connected to the controller 210 of system 100 when the tubing set is installed. The RFID or NFC tag (or barcode label) can be attached (e.g., molded into or adhered) to the tubing set at location along the tubing such that the tag aligns with an RFID or NFC reader 280 incorporated in the pump assembly 200 or on the IV pole 110 and enables the controller 210 through the reader 280 to read the tag 180. The pump assembly 200 can be labeled and molded (e.g., with a channel, groove or guide) to facilitate positioning the tubing 140 for proper operation. Optionally, a clip for the tubing 140 can be included on the outside of the pump assembly to position the tag 180 adjacent the reader 280 in pump assembly 200. The tag 180 can include information (e.g., data values and codes in memory of the tag) that identify the tube set 140 and can be used by the controller 210 to configure the system 100 for a predefined surgical procedure associated with one or more of the data values or codes received from the RFID or NFC tag 180. The tag's 180 data values and codes can include information regarding tube set expiration, reordering, batch information, and unique serial numbers for each tube set so the tube set cannot be reused for other procedures. The data values and codes can include system 100 configuration settings including the preferred pressure and temperature settings for a predefined surgical procedure as well as system 100 limits that define the maximum and/or minimum temperature and/or pressure readings that result in an alarm sounding or the system shutting down. Similarly, where the tube set 140 includes a barcode 180, the barcode 180 can be positioned to align with a barcode reader that provides information to the controller to configure the system for a predefined surgical procedure. In accordance with some embodiments of the invention, the RFID tag, the NFC tag or the barcode 180 can provide data or codes that can be used as an entry in an index or lookup table that specifies one or more system configuration settings (e.g., including operational limits and ranges) for a predefined surgical procedure or a surgical discipline (e.g., Urology, Orthopedics, Gynecology, etc.) associated with the tube set 140. The system 100 configuration settings can include the preferred pressure and temperature settings for a predefined surgical procedure as well as system 100 limits that define the maximum and/or minimum temperature and/or pressure readings that result in an alarm sounding or the system shutting down.

Figure 5:
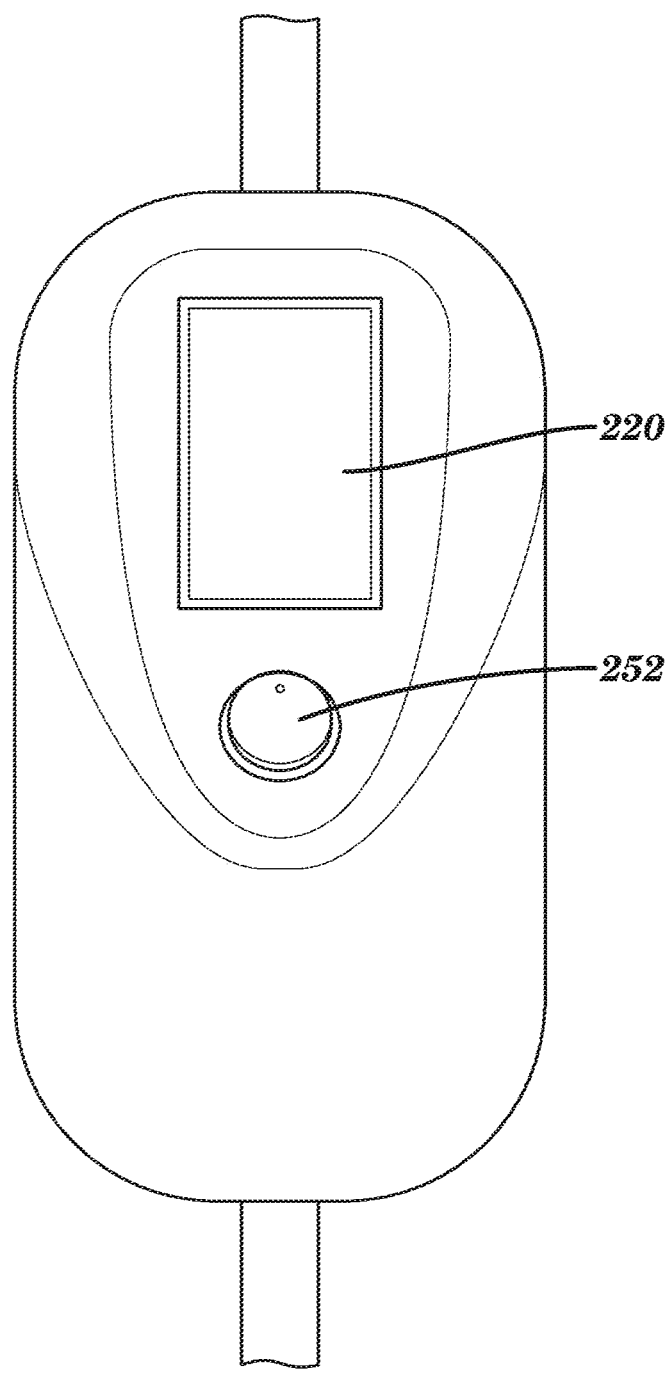
FIG. 5 is a front view of the pump assembly.
Figure 6:
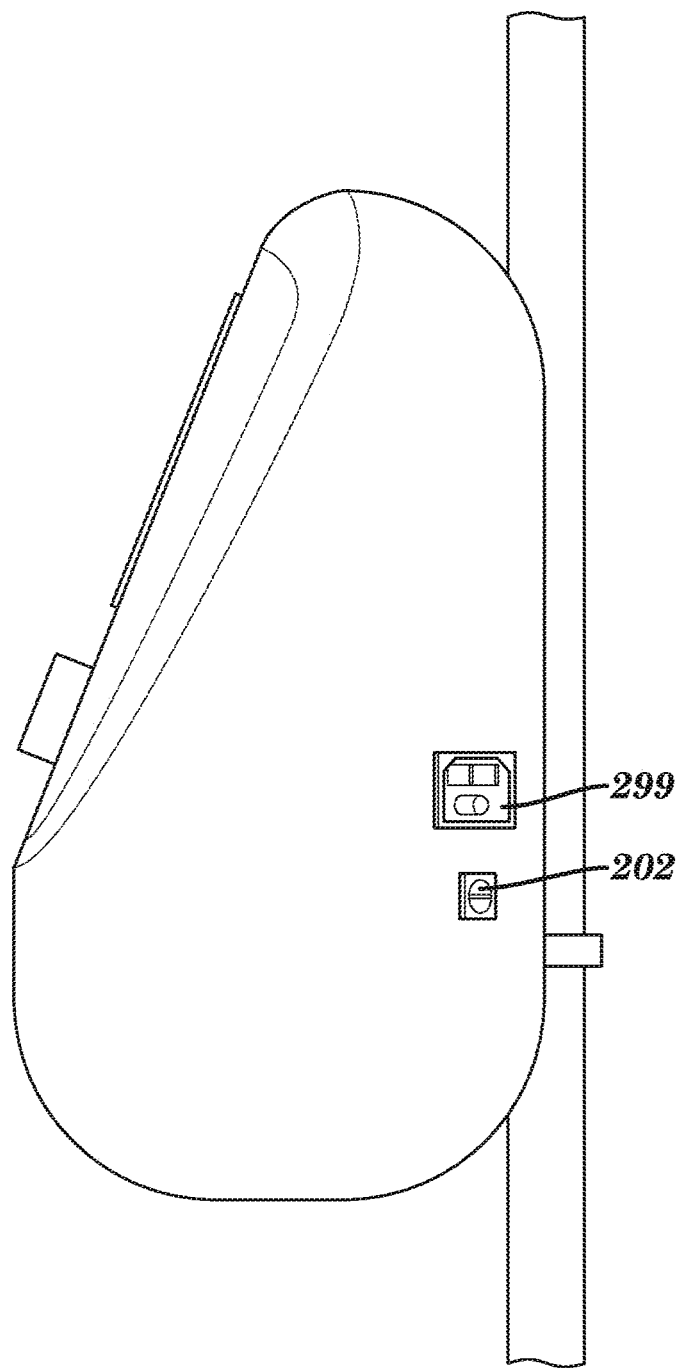
FIG. 6 is a side view of the upper part of the pump assembly.

As shown in FIGS. 5 and 6, the pump assembly 200 can be supported by or mounted on an IV pole 110 or other support structure. The pump assembly 200 component can be enclosed in a house as shown with the display 220 and the pressure regulator know 252 accessible on the front and a power cord connector 299 and a physical power switch 202 on the back at the base of the pump assembly 200 housing. The physical power switch 202 can include an on/off toggle switch that controls the flow of power to the system 100 by breaking connection between the AC/DC power transformer 290 and the wall out or breaking the connection to the battery.

After power is connected to the controller 210, either before or after initialization, the touch screen can optionally display the version of software and date on startup along with the company logo. In addition, a calibration countdown is also displayed to identify to the user number uses left until mandatory calibration. And, a tubing set countdown can be displayed to reminder the operator to reorder tubing sets.

In operation, after the RFID, NFC or barcode tag 180 is read by the reader 280, the reader 280 transfers the data to the controller 210. The software in the controller 210 can be configured to setup the software that controls the system 100 for a predefined surgical procedure as well as control the touch screen display to prompt the user for any additional information relating to the specific procedure/tubing set installed. The software in the controller 210 can include (or have access to) data tables that identify configuration setting for a given tube set 140. For example, the RFIC, NFC or barcode tag can provide numerical value that is uniquely associated with specific surgical procedure (e.g., hysteroscopic polyp removal) and that numerical value can be used as an index to a table stored in the memory of the controller 210. The controller 210 can obtain the preferred pressure (e.g. 180 mm Hg) and temperature (e.g., 98 deg. F.) settings from the table and set these as the default settings of the system. In addition, one or more fields in the table can be used to setup the display configuration, for example, in a surgical procedure where intravasation is a concern, the controller 210 can be configured to calculate fluid lost as a function of the fluid dispensed and fluid collected and the display can be configured to display the calculated fluid loss during the procedure. In addition, the controller 210 can also set a fluid loss threshold that triggers an alarm. The fluid loss threshold can be a predefined value or can be calculated by prompting the user to input information (e.g., patient weight or other physical characteristics) that can be used to calculate the fluid loss threshold.

In accordance with some embodiments of the invention, the tag 180 can be molded into one or more of the spikes of the tubing set and the reader 280 can be located in the fluid bag chamber 300 in close proximity to the base of the saline bag 130 spike port so it can be read by the system controller 210. Similarly, each bag of consumables (e.g., drape and tubing sets) used during the procedure can include a tag 180 and the fluid bag chamber 300 or the pump assembly 200 can include a reader 208 that collects information about these components from their respective tags 180, for example, when the user positions the tag 180 near the pre-identified location of the reader 280.

In accordance with some embodiments of the invention, the tag 180 can be on or in the packaging and/or the tubing and drape set and the entire package contents can be part of a "lot #" and scanned at the beginning of each procedure. The lot # information can be used for tracking of the entire contents of the package and could involve tracking different sets of information if, for example, the package includes components that may or may not be used depending upon the needs of the procedure. For example, the tubing sets 140 can be provided individually or as part of a combined package (e.g., a "deluxe package") that can include additional components such as a drape 175 and a suction tube set 160.

In accordance with some embodiments of the invention, the tags can include lot number information that can be used to facilitate order management. For example, each box or package of consumables (e.g., tube sets 130) can be identified with a sequence number, such as "3 of 10." And the system can be configured to only permit the consumables to be used in sequence (e.g., items "1 of 10" and "2 of 10" must be used before item "6 of 10"). Alternatively, as the consumables get used, the system can record instances each time a lot number is used and when the number of consumables from a given lot reaches a threshold (e.g. 7 out of a lot of 10), the controller can display a prompt to the user to remind the user to "reorder supplies—currently using 7 of 10". This prompt can either be ignored by pressing "remind me later" or confirmed by pressing "order has been placed". In addition, each tag can include an item serial number that can be stored in the memory of the controller 210 and prior to use, the controller 210 check the item serial number of the tube set 130 after it is installed to confirm (e.g., by comparing the item serial number with those stored in memory) that it is not match the item serial number from a prior procedure to prevent it from being reused.

Figure 13:
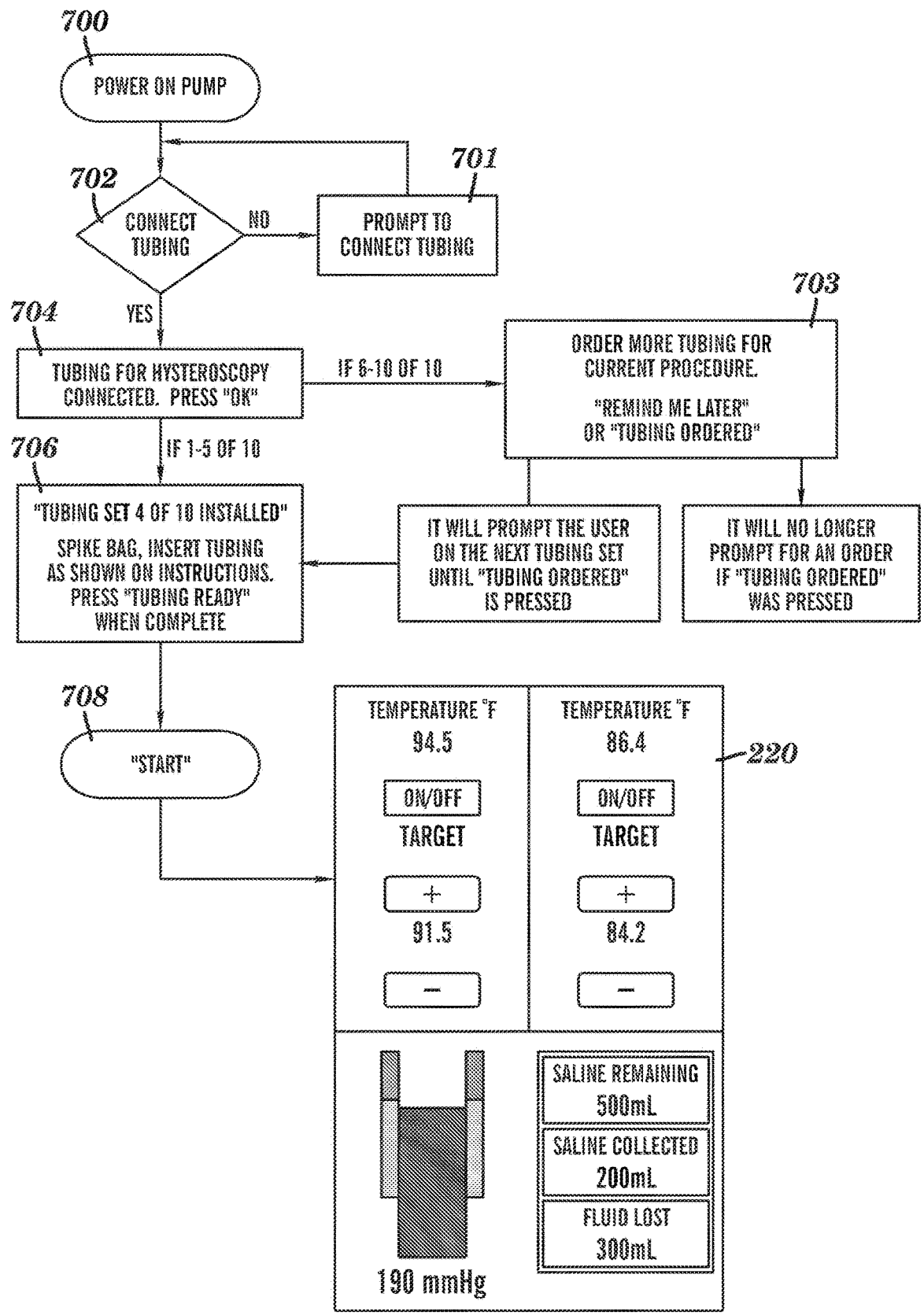
FIG. 13 is a flow diagram of an infusion system according to an embodiment of the present invention.

In accordance with some embodiments of the invention, as shown in FIG. 13, after the system 100 is powered on (at 700) either by plugging the device in or turning on the power switch, the controller 210 can initialize itself and present an initial display (e.g., with a "Start" button icon) to the user. After initialization, the controller 210 can check (at 702) whether the tube set 140 is connected by reading the RFID/NFC/Barcode 180 on the tubing. If the tubing is not connected, the controller 210 can configure the display 220 to prompt the user to install the tubing set 140 (at 701) and read RFID/NFC/Barcode to configure the system 100. Alternatively, the controller 210 can figure the display 220 to prompt the user to select a predefined procedure (e.g., from a menu) and then present a menu of possible tubing sets 140 that have been designed for the selected procedure. The display 220 can provide tube set ordering and supplier contact information as well. After the user installs the appropriate tube set 140 and presses the OK button icon (at 704), the controller 210 can read the RFID/NFC/Barcode 180 and begin the configure the system 100. During the configuration of the system 100, the controller 210 through software can evaluate the inventory levels to determine whether to prompt the user to order tubing. If the number of the tube set from the lot number and size is greater than a predefined threshold (e.g., number 5 of a lot size of 10), the controller 210 can configure the display 220 to prompt the user to order tubing (at 703). The controller 210 can be configured to display one or more user responses including a "tubing ordered" icon or a "remind me later" icon. If the tubing ordered icon is selected, the controller 210 notes in memory that tubing for the current lot number has been reordered. If the remind me later icon is selected, the system will remind the user to order tube sets the next time a tube set from the same lot number is installed. In the next step, the controller 210 configures the display 220 to display the start button (at 708). If the number of the tube set from the lot is less than a predefined threshold (e.g., number 5 of a lot size of 10), the controller 201 can configure the display 220 to instruct the user (at 706) to spike the fluid bag 130 and the press the tubing ready button icon on the screen. After the user presses the tubing ready icon, configures the system and presents the start button icon on the display 220. At this point, the user can open any valves and removed any claims in the tube set 140 in preparation for the procedure. The user can press the Start button (at 708) on the touch screen to turn the pump on and force the air bladder to expand to the preset pressure causing the fluid to flow from the fluid bag 130 to prime the tubing 140 to remove the air in preparation for the procedure. Once the procedure begins, the pressure can be maintained by the regulator and the pump will intermittently turn on when needed to maintain the appropriate pressure (typically between 10-15 psi) in the accumulation tank to support the procedure. The touch screen can continue to display the fluid temperature, volume and pressure and present touch controls on the screen to enable the user to one or more of the fluid temperature, volume, and pressure. In accordance with some embodiments, the touch screen can also display tubing information or provide a touch screen control (e.g., a button or other icon) when pressed displays information about the tube set 140 (e.g., from the RFID, NFC, or barcode) and optionally, other attached components such as the suction tube set, the drape, and the waste collection container 170, In accordance with some embodiments, the pressure adjustment control knob 252 can be positioned below the touch screen display 220 and the controller 210 can configure the display 220 to how the actual (e.g., measured) pressure in mmHg. The control knob 252 can be used to adjust the set pressure produced by the pressure regulator 250 to the air bladders 310. In accordance with some embodiments of the invention, a pressure sensor 262 can be connected the the regulated side of the air supply between the pressure regulator 250 and air bladder 310. Pressure sensor 262 can be connected to the controller 210 to provide the air pressure measurement that is displayed on the touch screen.

In accordance with some embodiments of the invention, the touch screen 220 can provide touch screen controls to control some or all components of the pump assembly 200. For example, the touch screen can include a touch "run/stop" button for initial heating and pump operation to reach the initial settings. In accordance with some embodiments of the invention, the touch screen 220 can be configured to any information that is useful to the user during the procedure. For example, the display can be configured to display the amount of fluid remaining in the fluid bag 130 so that it is visible at all times. The amount of fluid remaining in the fluid bag can be determined using the volume sensors or flow sensors. In accordance with some embodiments of the invention, the display can also be configured to shows the fluid deficit calculated as the difference between fluid used and fluid collected via the outflow or suction tubing. In accordance with some embodiments of the invention, touch screen controls can be available to adjust the fluid temperature and a dial or knob 252 can be used to adjust the fluid/air pressure inside the fluid bag chamber 300. A digital display can be used to show the preset recommended pressure and temperature limits based on the detected tag 180. The range display can vary based on predetermined "safe" operating limits of tubing and surgical tools used. If the safe limits are exceeded an alarm can be programmed to sound warning the operator that an adjustment may need to be made.

In accordance with some embodiments of the invention, the operator can adjust the fluid temperature using "+" and "−" button icons presented on the touch screen. The buttons can be configured to cycle the system through a set of preset temperatures, typically in the range of from 98° F. to 102° F. The touch screen can display the actual and the set temperatures of the fluid to the user. Optionally, a graphical color change (e.g., green) of the displayed temperature can be shown and/or audible beep can be provided when the actual (e.g., measured) value matches the set value. Similarly, the displayed temperature can change to color (e.g. to red) when the temperature exceeds a predefined or set threshold.

In accordance with some embodiments of the invention, the fluid pressure can be set with a physical knob 252 connected to the pressure regulator 250. The pressure can be adjustable in increments of <10 mmHg over a range of from 0 mmHg to 250 mmHg. In accordance with some embodiments, the air bladder 310 can be deflated by opening a relief valve 262 that allows the air to be released from the air bladder 310 and then the operator can push on the bladder to remove any excess air. The relief valve 262 can be closed after a full fluid bag 130 is installed in the fluid bag chamber 300 in preparation for use. The relief valve 264 can be connected between the pressure regulator 250 and the air bladder 310 to deflate the air bladder to replace the fluid bag 130. The relief valve 264 can also be used as an emergency release valve to relieve the pressure in the air bladder 310 if the sensor 262 measures a pressure that exceeds a predefined limit, for example, the controller 210 can automatically open the relief valve 264. The relief valve 264 can be opened by pressing a button icon, such as an emergency stop icon on the display panel 220. Alternatively, a mechanical button or electronic button can be directly connected to the relief valve 264 to open the valve 264 in the event of an emergency.

In accordance with some embodiments, the controller 210 can maintain set values for pressure, volume, and temperature throughout the surgical or diagnostic procedure, displaying the actual (e.g., measured) and set values for the temperature, volume, and the pressure on the touch screen throughout the procedure. If the measured temperature, volume, and/or pressure are not the same as the set values within a preset tolerance, an alarm can be configured to sound (beep). The alarm can be configured in the software of the controller 210 and utilize preset thresholds programmed in the firmware of the controller 210 or a lookup table stored in memory of the controller 210. The pressure can be adjusted mechanically using the pressure regulator 250, and an electric pressure sensor 262 can be connected between the pressure regulator 250 and the air bladder 310. The signals from the pressure sensor 262 can be used to determine the pressure value that is displayed on the display screen 220. The signals from the pressure sensor 262 can be used by the system 100 software in the controller 210 to monitor and control the operation of the system 100 during the procedure. For example, the measured pressure can be used, along with physical characteristics of the tube set 140 and the tool 150 (e.g., internal tube diameter and tool flow characteristics) to calculate the fluid flow rate. This information can be compare to information received from flow sensors incorporated in the tube set and large differences can be cause the system to sound an alarm to warn the user.

The controller 210 can include a processor and associated memory to enable it to execute one or more programs that control the operation of the pump assembly 200 and the system 100. The memory can include volatile and non-volatile memory capable of storing information after the power is disconnected. The controller 210 can include a wired (e.g., Ethernet, USB) or wireless (e.g., WiFi, Bluetooth, Zigbee) connection to allow programs and information to be transferred between the controller 210 and other computerized devices. The controller 210 can include an internal clock which can be used for logging and tracking events. The controller 210 can also compare the date and time of the procedure relative to the manufacturing date of the tubing set to ensure that the tube set has not expired.

The controller 210 can include a program or function that can log (e.g. store in non-volatile memory) some or all the information related to each specific procedure performed using the system 100. This information can include the date and start time of the procedure, some or all of the RFID, NFC or barcode data as well as some or all of the data retrieved look up tables using the RFID, NFC or barcode data, the tube set serial no., model no, manufacture date and expiration date, the number of fluid bags used, the fluid pressure, temperature and volume data at the start of the procedure and at periodic increments during the procedure through the end of the procedure, and information about the system 100 such as manufacture date, software versions, maintenance status. For example, the fluid pressure, temperature and volume data can be logged (or recorded) with a time stamp or the start time can be used and the fluid pressure, temperature and volume data can be logged at predefined time increments, such as every 1.0 sec., 2.0 sec., 5.0 sec., 10 sec., 15 sec., 30 sec., 1 min., 5 min., 15 min. or longer. Any of this information can be transmitted to the user institution (e.g., hospital or clinic) to enable them to track the settings that were used for a particular procedure. Some useful values that may be of interest include the amount of fluid used over a given timeframe and the entire procedure, information about any spikes in pressure or, drops in pressure over time (e.g., as an indication of a perforation). This information can be useful in determining a measure of fluid volume consumed over time and the entire procedure.

The logged information can also be used by a maintenance program in the controller to display to the user that one or more components of the system needs service (e.g., a pump diaphragm or seal needs to be replaced, an air bladder or regulator or component thereof needs to be replaced). This information can be transmitted by wire (e.g., Ethernet or USB) or wirelessly (e.g., WiFi, Bluetooth, Zigbee, cellular) to an institutional information technology system for archival storage and to update or confirm inventory management system information.

In accordance with some embodiments of the invention, the logged information can be wirelessly connected (via Bluetooth or other means) or hardwired to a compact thermal printer allowing the operator to print the values recorded in the procedure for review at a later date or to be used for tracking, insurance or liability purposes.

In accordance with some embodiments of the invention, the system can include a flow rate alarm that is configured by the software of the controller 210 to sound if certain conditions are met. For example, the system 100 can include operating parameters such as the fluid pressure and volume needed to maintain distention during a procedure. The software can be configured to monitor the fluid pressure and flow volume and compare it to the known or expected operating parameters (e.g., retrieved from memory or from the RFID, NFC or barcode data) for the tube set or the procedure. But if there is a spike or drop in the fluid flow and/or fluid pressure that is greater than a predefined threshold (e.g., 10%, 20%, 30%, 40%, 50%, or more) for longer than a predefined period of time (e.g., 1 sec., 2 sec., 5 sec., 10 sec., 15 sec., 20 sec., 30 sec., or more) the system software could sound an alarm alerting the user of a potentially abnormal condition. In accordance with some embodiments of the invention, the fluid flow and/or pressure thresholds and the predefined period of time can calculated using one or more algorithms or determined empirically. The algorithms can be stored in the memory of the controller 210 and can be "looked up" using the tubing set information.

In accordance with some embodiments of the invention, the alarm can alert the user to a potentially dangerous condition wherein the organ (e.g., the uterus) has become perforated. The alarm triggered by this particular set of conditions can have a unique sound, pitch and/or pattern to alert the user of the potentially dangerous condition. For example, in response to the special alarm, the user can inspect the surgical site to determine if an abnormal volume of the fluid leaked out during the procedure causing the abnormal condition and if so, clear the alarm. However, if the alarm sounds and there is no visible fluid leak, the user could take action to avoid the potentially dangerous condition from harming the patient. This would require calculations for a drop or increase respectively in "fluid pressure versus time" or "volume versus time".

In accordance with some embodiments of the invention, the system can include a temperature alarm will sound if the set temperature and actual temperature differ by a preset amount, for example, 3° F., or if the actual temperature is above the maximum set point. The temperature sensor is on the opposite side of the saline bag. In the case of an empty bag the sensor would heat up quickly and keep the bag from getting too hot. The temperature is measured via a thermocouple and is directly connected to the controller via software. The heating element turns on if the sensor does not detect the max temp has been me. Alternatively the sensor will turn off the heating element if the temperature has been satisfied.

In accordance with some embodiments of the invention, the system can include one or more Emergency Stop features. The pump assembly can include an Emergency Stop (button) on the front that is easily accessible by the user. Further, the controller can be configured with an Emergency Stop function that is automatically executed if certain conditions are met, for example, an alarm (e.g., over temperature or over pressure) continues for more than a predefined period of time. When the emergency stop is executed (either pressing the button or as a controller function) the system can also activate a solenoid or a relay to immediately remove air pressure (e.g., turn off power to the pump and open any pressure release valves) and turn off the heating elements. For example, this can also be initiated by the controller and set to be activated when the pressure threshold is approximately 25 mmHg higher than the set point. This difference can be ignored for a predefined period of time when the pressure is adjusted. This will prevent false triggers to active an alarm.

In accordance with some embodiments of the invention, the system 100 can also include a vacuum source that is connected to the tool 150 and a surgical drape 170 that can be used to draw waste fluid into a collection container 175. In accordance with some embodiments of the invention, the vacuum or suction can be produced by a vacuum pump 420 (e.g., a diaphragm pump) that can be connected to a vacuum accumulator tank 425 that provides suction (e.g., up to 400 mm Hg or more) at a port 427 on the pump assembly 200. In accordance with some embodiments of the invention, the vacuum or suction can be produced by a vacuum pump 420 (e.g., a diaphragm pump) that can be directly connected to the suction port 427 on the pump assembly 200. In accordance with some embodiments of the invention, the a pressure regulator can be connected between the vacuum pump or vacuum accumulator tank and the suction port 427 to regulate the vacuum pressure to the suction port 427. In accordance with some embodiments of the invention, the a flow restrictor or vacuum relief port/valve can be connected between the vacuum pump or vacuum accumulator tank and the suction port 427 to regulate the vacuum pressure to the suction port 427. In accordance with some embodiments of the invention, a vacuum pump 420 (with or without a connected vacuum accumulator tank 425) can be housed in the base 400 of the IV pole 110 and provide suction at a port 427 on the base 400 housing. The port 427 can be connected to a collection reservoir 175 and then to the surgical tool 150 and surgical drape 170 by a suction tube set 160. The suction tube set 160 enables the system 100 to draw waste fluid out of surgical site through the tool 150 and from the drape 170. The surgical tube set 160 can include a valve 164 at the tool 150 and a valve 166 at the drape 170 to selectively control the collection of waste fluid at those respective locations. The surgical tube set 160 can also include a valve 162 between the suction port 427 and the collection reservoir 175 to control the suction applied to the collection reservoir 175. The collection reservoir 175 can include a filter sock 176 to filter and collect tissue and debris for later analysis.

In accordance with some embodiments, the vacuum pump 420 can be run continuously to maintain vacuum pressure in the collection reservoir 175. The pump 420 can include a vacuum sensor 422 connected to the port 427 that can be configured to cut the power to the pump if a preset vacuum pressure is reached. The pump 420 can be configured to operate only when there is a drop in vacuum below a predefined vacuum pressure (e.g., −5 psi). When a diaphragm pump is used, the vacuum can be maintained without the need for the pump 420 to run constantly. The suction tube set 160 can include one or more flow sensors 172 that can be connected to the controller 210 and send fluid flow data to the controller 210. Software running on the controller 210 can track the fluid volume collected in memory and configure the display screen 220 to display the volume of fluid collected. The software running on the controller 210 can be configured to continuously or periodically recalculate and update the display of the volume of fluid collected.

In accordance with some embodiments of the invention, the collection reservoir 175 can be on a scale that continuously weighs the collection reservoir 175 as it is filled with fluid. The weight can be sent to the controller 210 and software running the controller 210 can determine the weight of the fluid (by subtracting the weight of the empty reservoir) and volume of the fluid from the density of the fluid (e.g., saline). As the reservoir fills with fluid, the controller 210 can continuously or periodically update its calculation of the volume and update the display 220. In accordance with some embodiments of the invention, the collection reservoir 175 can be graduated to enable the operator to visually see how much fluid has been collected.

In accordance with some embodiments of the invention, the system 100 can include a funneled drape 170 that collects the fluid that leaks from the surgical site. One of the suction tubes 160 can be connected to base of the drape where the fluid collects to sucked into the tube 160 and drawn into the collection reservoir 170. The collected tissue can be filtered and collected into the filter sock 176. In operation, the pump 420 can cycle on and off to maintain the desired suction. Once the procedure is complete the solids collected in the filter sock 176 can be sent to a lab for analysis.

In accordance with some embodiments of the invention, a single pump can be used to produce both air pressure and vacuum by selectively connecting (e.g., using valves controlled by the controller 210) the inflow port of the pump to a suction accumulator tank 425 and selectively connecting (e.g., using valves controlled by the controller 210) the outflow port of the pump to the air accumulator tank 240. In operation, the controller 210 can charge each accumulator tank with a predefined amount of air pressure and vacuum. The predefined amount can be sufficient to operate the system 100 without the need to use the pump during the procedure. The software in the controller 210 can monitor the accumulator tank pressures and anticipate the needs for air pressure and/or vacuum and selectively operate the pump to increase the air or vacuum pressure as needed.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:
1. A fluid infusion system, comprising:
 a pump assembly configured to pump fluid from a fluid bag, the pump assembly including a controller and a reader; and
 tubing fluidly interconnecting the fluid bag with a surgical tool such that fluid pumped from the fluid bag by the pump assembly flows through the tubing to the surgical tool, the tubing including a tag storing data, the tag storing data configured to be externally readable by the reader, wherein the reader of the pump assembly is configured to read the data from the tag of the tubing, and wherein the controller is configured to control the pumping of fluid from the fluid bag based at least in part on the data.

2. The fluid infusion system according to claim 1, wherein one of: the tag is an RFID tag and the reader is an RFID reader, the tag is an NFC tag and the reader is an NFC reader, or the tag is a barcode tag and the reader is a barcode reader.

3. The fluid infusion system according to claim 1, wherein the controller is configured to control the pumping of the fluid at least by determining whether or not fluid can be pumped through the tubing based at least in part on the data.

4. The fluid infusion system according to claim 3, wherein the data includes at least one of: expiration information, batch information, or unique serial number information.

5. The fluid infusion system according to claim 1, wherein the controller is configured to control the pumping of the fluid by setting a fluid pressure based at least in part on the data.

6. The fluid infusion system according to claim 1, further comprising a heater configured to heat the fluid pumped from the fluid bag.

7. The fluid infusion system according to claim 6, wherein the controller is configured to control the pumping of the fluid by setting a fluid temperature based at least in part on the data.

8. The fluid infusion system according to claim 1, wherein the data includes operational limits or ranges, and wherein the controller is configured to control the pumping of fluid from the fluid bag based at least in part on the operational limits or ranges.

9. The fluid infusion system according to claim 1, wherein the data includes a surgical discipline, and wherein the controller is configured to control the pumping of fluid from the fluid bag based at least in part on the surgical discipline.

10. The fluid infusion system according to claim 9, wherein the surgical discipline is one of: urology, orthopedics, or gynecology.

11. The fluid infusion system according to claim 1, wherein the tubing includes a spike configured to facilitate fluid connection of the tubing with the fluid bag.

12. The fluid infusion system according to claim 11, wherein the tag is attached to the spike.

13. The fluid infusion system according to claim 12, wherein the tag is adhered to or molded into the spike.

14. The fluid infusion system according to claim 1, wherein the tag is adhered to or molded into the tubing.

15. The fluid infusion system according to claim 1, wherein the pump assembly includes a receiver configured to receive a portion of the tubing including the tag such that the tag is operably positioned relative to the reader to enable reading of the data.

16. The fluid infusion system according to claim 15, wherein the receiver is a clip.

17. The fluid infusion system according to claim 15, wherein the receiver is a channel, groove, or guide.

18. The fluid infusion system according to claim 1, wherein the pump assembly includes a fluid bag chamber configured to receive the fluid bag and an inflatable bladder disposed within the fluid bag chamber, and wherein the controller is configured to control the pumping of fluid from the fluid bag by selectively inflating the inflatable bladder.

19. The fluid infusion system according to claim 1, wherein the pump assembly includes a display and wherein the controller is configured to output information for display on the display based at least in part on the data.

* * * * *